(12) United States Patent
Petersen et al.

(10) Patent No.: US 11,304,608 B2
(45) Date of Patent: Apr. 19, 2022

(54) METHOD AND APPARATUS OF MONITORING FOOT INFLAMMATION

(71) Applicant: Podimetrics, Inc., Somerville, MA (US)

(72) Inventors: Brian Petersen, Somerville, MA (US); Jonathan David Bloom, Medford, MA (US); David Robert Linders, Waltham, MA (US); Jeffrey Mark Engler, Cambridge, MA (US)

(73) Assignee: Podimetrics, Inc., Somerville, MA (US)

( * ) Notice: Subject to any disclaimer, the term of this patent is extended or adjusted under 35 U.S.C. 154(b) by 458 days.

(21) Appl. No.: 15/144,658

(22) Filed: May 2, 2016

(65) Prior Publication Data
US 2016/0256056 A1   Sep. 8, 2016

Related U.S. Application Data

(63) Continuation of application No. 14/662,738, filed on Mar. 19, 2015, now Pat. No. 9,326,723, which is a
(Continued)

(51) Int. Cl.
*A61B 5/01* (2006.01)
*A61B 5/00* (2006.01)
(Continued)

(52) U.S. Cl.
CPC ............ *A61B 5/015* (2013.01); *A43B 3/0005* (2013.01); *A61B 5/0022* (2013.01);
(Continued)

(58) Field of Classification Search
CPC ........... A61B 5/015; A61B 5/01; A61B 5/447; A61B 5/0075; A61B 5/7282;
(Continued)

(56) References Cited

U.S. PATENT DOCUMENTS

| 3,970,074 | A | * | 7/1976 | Mogos | ................... G01K 13/20 |
| | | | | | 600/549 |
| 4,574,359 | A | | 3/1986 | Ishizaka et al. | .............. 364/557 |

(Continued)

FOREIGN PATENT DOCUMENTS

| CN | 1308225 | 8/2001 | ............... G01K 3/00 |
| CN | 201312800 | 9/2009 | ............... A61B 5/00 |

(Continued)

OTHER PUBLICATIONS

Bharara, Bharara, M-PI-Technology Summary, 5 pages, undated.
(Continued)

*Primary Examiner* — Rene T Towa
(74) *Attorney, Agent, or Firm* — Nutter McClennan & Fish LLP

(57) ABSTRACT

A method and apparatus for evaluating foot inflammation each uses at least one temperature detection modality to form a first thermogram and a second thermogram of the sole of at least one foot. Each thermogram forms a substantially continuous set of two-dimensional temperature values across the sole of the (at least one) foot. The thermograms have features; namely, the first thermogram has first features and the second thermogram has second features. The method and apparatus thus control a device to apply at least one transformation to the first and second thermograms to align the first features with corresponding second features, and determine, at any thermogram location, if at least one of the thermograms presents one of a plurality of patterns indicative of inflammation. Finally, the method and apparatus each produce output information indicating the result of the determination of whether the thermograms present one of the plurality of patterns.

15 Claims, 16 Drawing Sheets

Related U.S. Application Data continuation-in-part of application No. 13/799,828, filed on Mar. 13, 2013, now Pat. No. 92,591,788.

(60) Provisional application No. 61/968,696, filed on Mar. 21, 2014.

(51) Int. Cl.

| | |
|---|---|
| *A43B 3/00* | (2006.01) |
| *G16H 40/63* | (2018.01) |
| *G16H 50/30* | (2018.01) |
| *G16H 50/20* | (2018.01) |
| *G16H 30/40* | (2018.01) |
| *A61B 5/103* | (2006.01) |

(52) U.S. Cl.
CPC ............ *A61B 5/0075* (2013.01); *A61B 5/445* (2013.01); *A61B 5/447* (2013.01); *A61B 5/4887* (2013.01); *A61B 5/6802* (2013.01); *A61B 5/6807* (2013.01); *A61B 5/6829* (2013.01); *A61B 5/6892* (2013.01); *A61B 5/7275* (2013.01); *A61B 5/7282* (2013.01); *G16H 30/40* (2018.01); *G16H 40/63* (2018.01); *G16H 50/20* (2018.01); *G16H 50/30* (2018.01); *A61B 5/0008* (2013.01); *A61B 5/0077* (2013.01); *A61B 5/103* (2013.01); *A61B 5/7203* (2013.01); *A61B 5/725* (2013.01); *A61B 5/7246* (2013.01); *A61B 5/7253* (2013.01); *A61B 2562/0271* (2013.01); *A61B 2576/02* (2013.01)

(58) Field of Classification Search
CPC ..... A61B 5/6802; A61B 5/4887; A61B 5/445; A61B 5/7275; A61B 5/0022; A61B 5/6892; A61B 2562/0271; A61B 2576/02; A61B 5/0008; A61B 5/6829; A61B 5/103
See application file for complete search history.

(56) References Cited

U.S. PATENT DOCUMENTS

| | | | |
|---|---|---|---|
| 4,592,000 A | 5/1986 | Ishizaka et al. | 364/557 |
| 4,629,336 A | 12/1986 | Ishizaka | 374/169 |
| 4,647,918 A | 3/1987 | Goforth | 340/573 |
| 4,648,055 A | 3/1987 | Ishizaka et al. | 164/557 |
| 4,843,577 A | 6/1989 | Muramoto | 364/557 |
| 4,866,621 A | 9/1989 | Ono | 364/413.03 |
| 4,878,184 A | 10/1989 | Okada et al. | 364/557 |
| 5,011,294 A | 4/1991 | Yamaguchi | 374/107 |
| 5,015,102 A | 5/1991 | Yamaguchi | 374/107 |
| 5,066,141 A | 11/1991 | Ikeda et al. | 374/169 |
| 5,259,389 A | 11/1993 | Muramoto et al. | 128/736 |
| 5,473,629 A | 12/1995 | Muramoto | 374/102 |
| 5,642,096 A | 6/1997 | Leyerer et al. | 340/573 |
| 5,678,566 A | 10/1997 | Dribbon | 128/779 |
| 5,929,332 A | 7/1999 | Brown | 73/172 |
| 6,090,050 A * | 7/2000 | Constantinides | A61B 5/447 374/100 |
| 6,195,921 B1 | 3/2001 | Truong | 36/136 |
| 6,398,740 B1 * | 6/2002 | Lavery | A61B 5/015 128/903 |
| 6,767,330 B2 | 7/2004 | Lavery et al. | 600/549 |
| 6,807,869 B2 | 10/2004 | Farringdon et al. | 73/862.046 |
| 6,963,772 B2 | 11/2005 | Bloom et al. | 600/547 |
| 7,052,472 B1 | 5/2006 | Miller et al. | 600/549 |
| 7,167,734 B2 | 1/2007 | Khalil et al. | 600/310 |
| 7,206,718 B2 | 4/2007 | Cavanagh et al. | 702/155 |
| 7,318,004 B2 | 1/2008 | Butterfield | 702/130 |
| 7,637,657 B2 | 12/2009 | Yamamoto et al. | 374/169 |
| 7,716,005 B2 | 5/2010 | Shoureshi et al. | 702/131 |
| 7,726,206 B2 | 6/2010 | Terrafranca, Jr. et al. | 73/862.041 |
| 7,758,523 B2 | 7/2010 | Collings et al. | 600/592 |
| 8,360,987 B2 | 1/2013 | Kantro et al. | 600/549 |
| 2002/0082486 A1 * | 6/2002 | Lavery | A61B 5/01 600/300 |
| 2006/0021261 A1 | 2/2006 | Face | 36/132 |
| 2006/0030783 A1 | 2/2006 | Tsai et al. | 600/547 |
| 2007/0038273 A1 | 2/2007 | Bales et al. | 607/88 |
| 2007/0039211 A1 | 2/2007 | Pichler | 36/140 |
| 2007/0043408 A1 | 2/2007 | Winnett et al. | 607/96 |
| 2008/0109183 A1 * | 5/2008 | Shoureshi | G01K 1/14 702/131 |
| 2008/0214962 A1 | 9/2008 | Kantro et al. | 600/592 |
| 2009/0219972 A1 | 9/2009 | Carlsson et al. | 374/137 |
| 2009/0306801 A1 | 12/2009 | Sivak et al. | 700/98 |
| 2010/0004566 A1 | 1/2010 | Son et al. | 600/592 |
| 2010/0041998 A1 | 2/2010 | Postel | 600/475 |
| 2010/0198022 A1 | 8/2010 | Vuillerme et al. | 600/301 |
| 2010/0268111 A1 | 10/2010 | Drinan et al. | 600/547 |
| 2010/0324455 A1 | 12/2010 | Rangel et al. | 600/592 |
| 2011/0015498 A1 * | 1/2011 | Mestrovic | A61B 5/14517 600/301 |
| 2011/0122251 A1 * | 5/2011 | Schmidt | G06K 9/2018 348/164 |
| 2011/0214501 A1 | 9/2011 | Ross et al. | 73/172 |
| 2011/0275956 A1 | 11/2011 | Son et al. | 600/592 |
| 2011/0313314 A1 | 12/2011 | Gefen | 600/555 |
| 2012/0020573 A1 * | 1/2012 | Kacenjar | G06T 3/0068 382/218 |
| 2012/0109013 A1 | 5/2012 | Everett et al. | 600/587 |
| 2012/0190989 A1 | 7/2012 | Kaiser et al. | 600/476 |
| 2012/0221286 A1 | 8/2012 | Bisch et al. | 702/131 |
| 2013/0019503 A1 | 1/2013 | Vogt | 36/103 |
| 2013/0162796 A1 * | 6/2013 | Bharara | A61B 5/0077 348/77 |
| 2013/0261495 A1 | 10/2013 | Linders et al. | |
| 2015/0057562 A1 | 2/2015 | Linders et al. | |
| 2015/0190059 A1 | 7/2015 | Petersen et al. | |
| 2015/0206301 A1 * | 7/2015 | Mestha | G01J 5/0025 382/128 |
| 2016/0256056 A1 | 9/2016 | Petersen et al. | |
| 2017/0188841 A1 | 7/2017 | Ma et al. | |

FOREIGN PATENT DOCUMENTS

| | | | |
|---|---|---|---|
| CN | 202263087 | 6/2012 | ............ A61F 7/00 |
| DE | 202010013176 | 3/2011 | ............ A61B 5/107 |
| EP | 0885587 | 12/1998 | ............ A61B 5/00 |
| EP | 1511419 B1 | 8/2008 | ............ A61B 5/103 |
| JP | 55071919 | 5/1980 | ............ G01K 1/02 |
| JP | H03-275039 A | 12/1991 | ............ A61B 5/00 |
| JP | H03-275039 A | 12/1991 | ............ A61B 5/00 |
| JP | 2002-269231 A | 9/2002 | ............ G06F 17/60 |
| JP | 2004-528085 A | 9/2004 | ............ A61B 5/00 |
| JP | 2005-533543 A | 11/2005 | ............ A61B 10/00 |
| JP | 2009-539454 | 11/2009 | ............ A61B 5/00 |
| JP | 2011508243 A | 3/2011 | |
| JP | 2013/151705 A | 8/2013 | |
| KR | 101027367 | 4/2011 | ............ A61B 5/145 |
| RU | 2433783 | 11/2011 | ............ A61B 5/01 |
| WO | WO 2007/114768 | 10/2007 | ............ G01K 11/12 |
| WO | WO 2008/058051 | 5/2008 | ............ G01K 13/00 |
| WO | WO 2009/005373 | 1/2009 | ............ A61B 5/01 |
| WO | WO 2010/021932 | 2/2010 | |
| WO | WO 2012/051394 | 4/2012 | |
| WO | 2012055029 A1 | 5/2012 | |
| WO | WO 2012/084814 | 6/2012 | |
| WO | WO-2013/151705 | 10/2013 | |

OTHER PUBLICATIONS

Bharara et al., "Coming events cast their shadows before: detecting inflammation in the acute diabetic foot and the foot in remission," Diabetes/Metabolism Research and Reviews, vol. 28, pp. 15-20, 2012.

Brioschi et al., "Automated Computer Diagnosis of IR Medical Imaging," FLIR Technical Series, Application Note for Research & Science, FLIR Systems, Inc., 2011.

(56) References Cited

OTHER PUBLICATIONS

Caselli et al., "The Forefoot-to-Rearfoot Plantar Pressure Ratio Is Increased in Severe Diabetic Neuropathy and Can Predict Foot Ulceration," Diabetes Care, vol. 25, No. 6, pp. 1066-1071, Jun. 2002.
Chen et al., "Development of a Thermal and Hyperspectral Imaging System for Wound Characterization and Metabolic Correlation," John Hopkins Apl Technical Digest, vol. 26, No. 1, pp. 67-74, 2005.
Dabiri et al., "Electronic Orthotics Shoe: Preventing Ulceration in Diabetics Patients," 30th Annual International IEEE EMBS Conference, pp. 771-774, Aug. 2008.
Kaabouch et al., "Predicting neuropathic ulceration: analysis of static temperature distributions in thermal images," Journal of Biomedical Optics, vol. 15, No. 6, pp. 061715-1-061715-6, Nov./Dec. 2010.
Liu et al., "Infrared Dermal Thermography on Diabetic Feet Soles to Predict Ulcerations: a Case Study," Proceedings of SPIE, vol. 8572, pp. 85720N-1-85720N-9, 2013.
Liu et al., "Statistical analysis of spectral data: a methodology for designing an intelligent monitoring system for the diabetic foot," Journal of Biomedical Optics, vol. 18, No. 12, pp. 126004-1-126004-11, Dec. 2013.
Medgadget.com, "TempTouch for Foot Ulcer Detection," Xilas, Inc., 2 pages, Apr. 19, 2005.
Morley et al., "In-Shoe Multisensory Data Acquisition System," IEEE Transactions on Biomedical Engineering, vol. 48, No. 7, pp. 815-820, Jul. 2001.
Roback, "An overview of temperature monitoring devices for early detection of diabetic foot disorders," Linkoping University Post Print, 18 pages, undated.
Van Netten et al., "Infrared Thermal Imaging for Automated Detection of Diabetic Foot Complications," Journal of Diabetes Science and Technology, vol. 7, No. 5, pp. 1122-1129, Sep. 2013.
Visual Footcare Technologies, LLC, "TempStat," Visual Footcare Technologies, LLC, Thermal Imagine Device, One unit: $125, 2 pages, undated.
Korean Intellectual Property Office, International Search Report—International Application No. PCT/US2013/030997, dated Jul. 8, 2013, together with the Written Opinion of the International Searching Authority, 13 pages.
European Patent Office, Supplementary European Search Report—Application No. EP 13 77 2800, dated Jun. 26, 2015, 7 pages.
Ammer et al., *Thermal Imaging of Skin Changes on the Feet of Type II Diabetics*, 2001 Conference Proceedings of the 23rd Annual International Conference of the IEEE Engineering in Medicine and Biology Society, Istanbul, Turkey, Oct. 25-28, 2001, 4 pages.
Armstrong et al., *Monitoring Healing of Acute Charcot's Arthropathy with Infrared Dermal Thermometry*, Journal of Rehabilitation Research and Development, vol. 34, No. 3, pp. 317-321, Jul. 1997.
Frykberg et al., *Feasibility and Efficacy of a Smart Mat Technology to Predict Development of Diabetic Plantar Ulcers*, Diabetes Care, vol. 40, pp. 973-980, Jul. 2017.
European Patent Office, Notice of Opposition to a European Patent—European Patent No. 2833783B1, dated May 31, 2018, 8 pages.
Japanese Patent Office, Decision of Refusal, Appl. No. 2016-558325, dated Sep. 2, 2019, 10 pages, together with English translation.
Chinese National Intellectual Property Administration, Office Action, Appl. No. 201580015377.7, dated Jan. 8, 2019, 9 pages.
Chinese National Intellectual Property Administration, Office Action, Appl. No. 201580015377.7, dated Aug. 16, 2019, 9 pages.
Liu C., et al., "Automatic detection of diabetic foot complications with infrared thermography by asymmetric anlysis," Journal of Biomedical Optics, vol. 20(2), (Feb. 2015), pp. 026003-1-026003-10 [11 pages].
Liu C., et al., "Infrared Dermal Thermography on Diabetic Feet Soles to Predict Ulcerations: a Case Study," Advanced Biomedical and Clinical Diagnostic System XI, vol. 8572, 85720N, downloaded from http://proceedings.spiedigitallibrary.org/ on Jul. 8, 2013 [9 pages].

\* cited by examiner

METHOD AND APPARATUS OF MONITORING FOOT INFLAMMATION

PRIORITY

This patent application is a continuation patent application of U.S. patent application Ser. No. 14/662,738, U.S. Pat. No. 9,326,723 on issue date May 3, 2016, filed Mar. 19, 2015, entitled, "METHOD AND APPARATUS OF MONITORING FOOT IMFLAMMATION," and naming Brian Petersen, Jonathan David Bloom, David Robert Linders, Jeffrey Mark Engler as inventors, which is a continuation-in-part of U.S. patent application Ser. No. 13/799,828, now U.S. Pat. No. 9,259,178, filed Mar. 13, 2013, entitled, "METHOD AND APPARATUS FOR INDICATING THE RISK OF AN EMERGING ULCER," and naming Jonathan David Bloom, David Robert Linders, Jeffrey Mark Engler, Brian Petersen, David Charles Kale, and Adam Geboff as inventors, and claims priority from provisional U.S. patent application No. 61/968,696, filed Mar. 21, 2014, entitled, "METHOD OF NORMALIZING AND ANALYZING DERMAL OR SUB-DERMAL DATA FOR MONITORING INFLAMMATION," and naming Brian Petersen, David Linders, Jeffrey Engler, and Jonathan Bloom as inventors.

All of the above listed patent documents (patents and applications) are incorporated herein, in their entireties, by reference.

RELATED APPLICATIONS

This patent application is related to the following utility patent applications, each of which is incorporated herein, in its entirety, by reference:

1. U.S. patent application Ser. No. 13/803,866, now U.S. Pat. No. 9,095,305, filed on Mar. 14, 2013, entitled, "METHOD AND APPARATUS FOR INDICATING THE EMERGENCE OF A PRE-ULCER AND ITS PROGRESSION," and naming Jonathan David Bloom, David Robert Linders, Jeffrey Mark Engler, Brian Petersen, David Charles Kale, and Adam Geboff as inventors, and 2. U.S. patent application Ser. No. 13/799,847, now U.S. Pat. No. 9,271,672, filed on Mar. 13, 2013, entitled, "METHOD AND APPARATUS FOR INDICATING THE EMERGENCE OF AN ULCER," and naming Jonathan David Bloom, David Robert Linders, Jeffrey Mark Engler, Brian Petersen, David Charles Kale, and Adam Geboff as inventors.

Both of the above listed patents are incorporated herein, in their entireties, by reference.

FIELD OF THE INVENTION

The invention generally relates to dermatological ulcers on living beings and, more particularly, the invention relates to evaluating portions of living beings for dermatological ulcers.

BACKGROUND OF THE INVENTION

Open sores on an external surface of the body often form septic breeding grounds for infection, which can lead to serious health complications. For example, foot ulcers on the bottom of a diabetic's foot can lead to gangrene, leg amputation, or, in extreme cases, death. The healthcare establishment therefore recommends monitoring the foot of a diabetic on a regular basis to avoid these and other dangerous consequences. Unfortunately, known techniques for monitoring foot ulcers, among other types of ulcers, often are inconvenient to use, unreliable, or inaccurate, thus reducing compliance by the very patient populations that need it the most.

SUMMARY OF VARIOUS EMBODIMENTS

In accordance with one embodiment of the invention, a method and apparatus for evaluating foot inflammation each uses at least one temperature detection modality to form a first thermogram and a second thermogram of the sole of at least one foot. Each thermogram forms a substantially continuous set of two-dimensional temperature values across the sole of the (at least one) foot. The thermograms have features; namely, the first thermogram has first features and the second thermogram has second features. The method and apparatus thus control a device to apply at least one transformation (e.g., an affine transformation, non-affine transformation, or a combination) to one or both of the first and second thermograms to align the first features with corresponding second features, and determine, at any thermogram location, if at least one of the thermograms presents one of a plurality of patterns indicative of inflammation. Finally, the method and apparatus each produce output information indicating the result of the determination of whether the thermograms present one of the plurality of patterns.

The at least one affine transformation may include, among other things, at least one of reflection, rotation, scaling and translation. The affine transformation preferably aligns the first features and the second features to a common coordinate system. The at least one affine transformation also may be applied to a set of points corresponding to a) foot temperature, b) a grid corresponding to foot temperature, or 3) a set of equations corresponding to foot temperature. In addition to applying the affine transformation(s), some implementations apply at least one non-affine transformation to the first and second thermograms.

The two thermograms may apply to a single foot, or both feet. Thus, the first thermogram may represent the sole a left foot of a given person, and the second thermogram represents the sole of a right foot of the given person. In that case, the method and apparatus each may use the modality to obtain temperatures across the sole of the left foot at a first time, and obtain temperatures across the sole of the right foot at a second time. The first time and second time may be different times. Alternatively, the first thermogram and the second thermogram may represent the sole of the same foot of a given person. In that case, the data used to form the first and second thermograms can be obtained at different times, or at substantially the same time.

The at least one temperature detection modality may include a thermal camera. In that case, a person may hold the thermal camera in an unconstrained manner in at least three degrees of freedom in free space when the thermal camera obtains temperature data of the sole of the at least one foot. For example, when the person is holding the camera, the camera is free to move in space (relative to the sole of the at least one foot) while the person holds the thermal camera and obtains the temperature data. The at least three degrees of freedom may include at least three of translational movement in the X-axis, the Y-axis, and the Z-axis of the Cartesian Coordinate System, and rotation about the X-axis, the Y-axis, and the Z-axis of the Cartesian Coordinate System. Other temperature detection modalities may include an insole in which the foot is positioned, and an open platform having a substrate for receiving the at least one foot, and a plurality of temperature sensors that are stationary relative to the substrate. Alternative embodiments may vary the position of the temperature sensors relative to the substrate.

The method and apparatus each may control a device to orient the first thermogram and the second thermogram to a common coordinate system by changing the orientation of at least one of the first and second thermograms for roll (rotation about the X-axis), pitch (rotation about the Y-axis), yaw (rotation about the Z-axis), X-axis translation, Y-axis translation, and Z-axis translation. Moreover, the at least one temperature detection modality may obtain a plurality of discrete temperature values of the sole of the at least one foot, and calculate temperatures between a plurality of adjacent discrete temperature values to form the thermograms of the sole of each of the at least one foot.

Some embodiments control the device to orient by retrieving the first thermogram from memory, and using the orientation of the first thermogram to orient the second thermogram. To improve accuracy in some instances, the apparatus and method each may normalize the amplitude of the two-dimensional array of temperature values of the first and second thermograms against a common value.

In accordance with another embodiment, a system for evaluating foot inflammation has a thermogram generator configured to form a first two-dimensional thermogram and a second two-dimensional thermogram of the sole of the at least one foot. Each thermogram forms a substantially continuous set of two-dimensional temperature values across the sole of the at least one foot. Moreover, the first thermogram and second thermogram have respective first and second features. The apparatus also has an orientation module operatively coupled with the thermogram generator and configured to apply at least one affine transformation to the first and second thermograms to align the first features of first thermogram with corresponding second features of the second thermogram. The apparatus further has a pattern recognition system operatively coupled with the orientation module and configured to determine, at any location within the first thermogram and the second thermogram, if the thermograms present one of a plurality of patterns indicative of inflammation. Finally, the apparatus has an analyzer operatively coupled with the pattern recognition system and configured to produce output information indicating the result of the determination of whether the thermograms present one of the plurality of patterns.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

In illustrative embodiments, an apparatus analyzes a patient's foot to determine the risk of an ulcer emerging on its underside (i.e., on its sole). This permits patients their healthcare providers and/or their caregivers to intervene earlier, reducing the risk of more serious complications. To that end, a modality detects foot temperatures to generate two or more thermograms. The apparatus then applies a transformation to the thermograms, normalizing/registering the thermograms so that they comply with a standard coordinate system. If the transformed thermogram presents at least one of a number of prescribed patterns, then various embodiments produce output information indicating the risk of an ulcer emerging on the patient's foot. Details of illustrative embodiments are discussed below.

Figure 1:
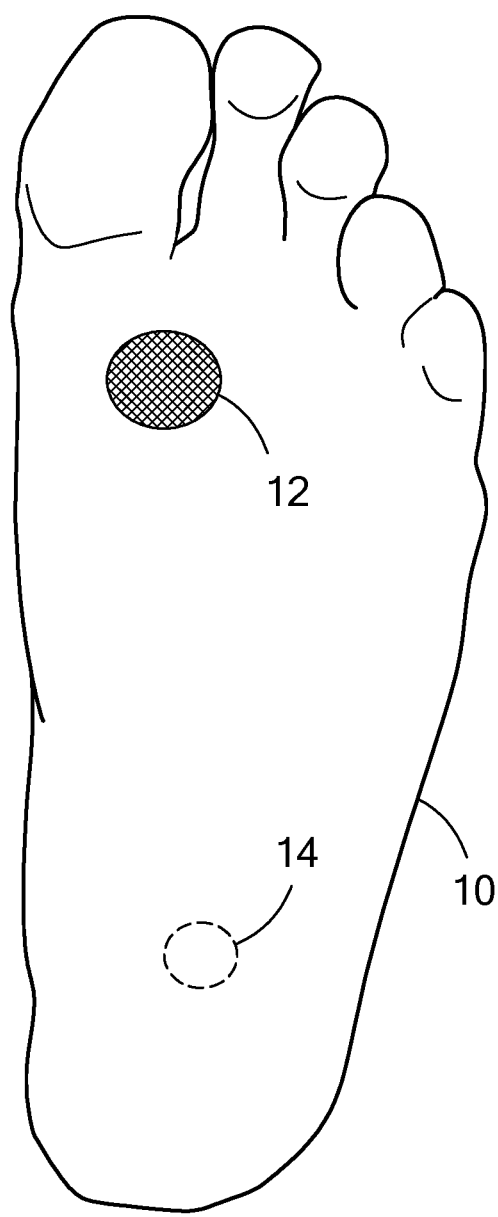
FIG. 1 schematically shows a foot having a prominent foot ulcer and a pre-ulcer.

FIG. 1 schematically shows a bottom view of a patient's foot 10 that, undesirably, has an ulcer 12 and a pre-ulcer 14 (described below and shown in phantom since pre-ulcers 14 do not break through the skin). As one would expect, an ulcer 12 on this part of the foot 10 typically is referred to as a "foot ulcer 12." Generally speaking, an ulcer is an open sore on a surface of the body generally caused by a breakdown in the skin or mucous membrane. Diabetics often develop foot ulcers 12 on the soles of their feet 10 as part of their disease. In this setting, foot ulcers 12 often begin as a localized inflammation that may progress to skin breakdown and infection.

It should be noted that discussion of diabetes and diabetics is but one example used simply for illustrative purposes only. Accordingly, various embodiments apply to other types of diseases (e.g., stroke, deconditioning, sepsis, friction, coma, etc. . . . ) and other types of ulcers—such embodiments may apply generally where there is a compression or friction on the living being's body over an extended period of time. For example, various embodiments also apply to ulcers formed on different parts of the body, such as on the back (e.g., bedsores), inside of prosthetic sockets, or on the buttocks (e.g., a patient in a wheel chair). Moreover, illustrative embodiments apply to other types of living beings beyond human beings, such as other mammals (e.g., horses or dogs). Accordingly, discussion of diabetic human patients having foot ulcers 12 is for simplicity only and not intended to limit all embodiments of the invention.

Many prior art ulcer detection technologies known to the inventors suffered from one significant problem—patient compliance. If a diseased or susceptible patient does not regularly check his/her feet 10, then that person may not learn of an ulcer 12 or a pre-ulcer 14 until it has emerged through the skin and/or requires significant medical treatment. Accordingly, illustrative embodiments implement an ulcer monitoring system in any of a variety of forms and modalities—preferably in an easy to use form factor that facilitates and encourages regular use.

Figure 2:
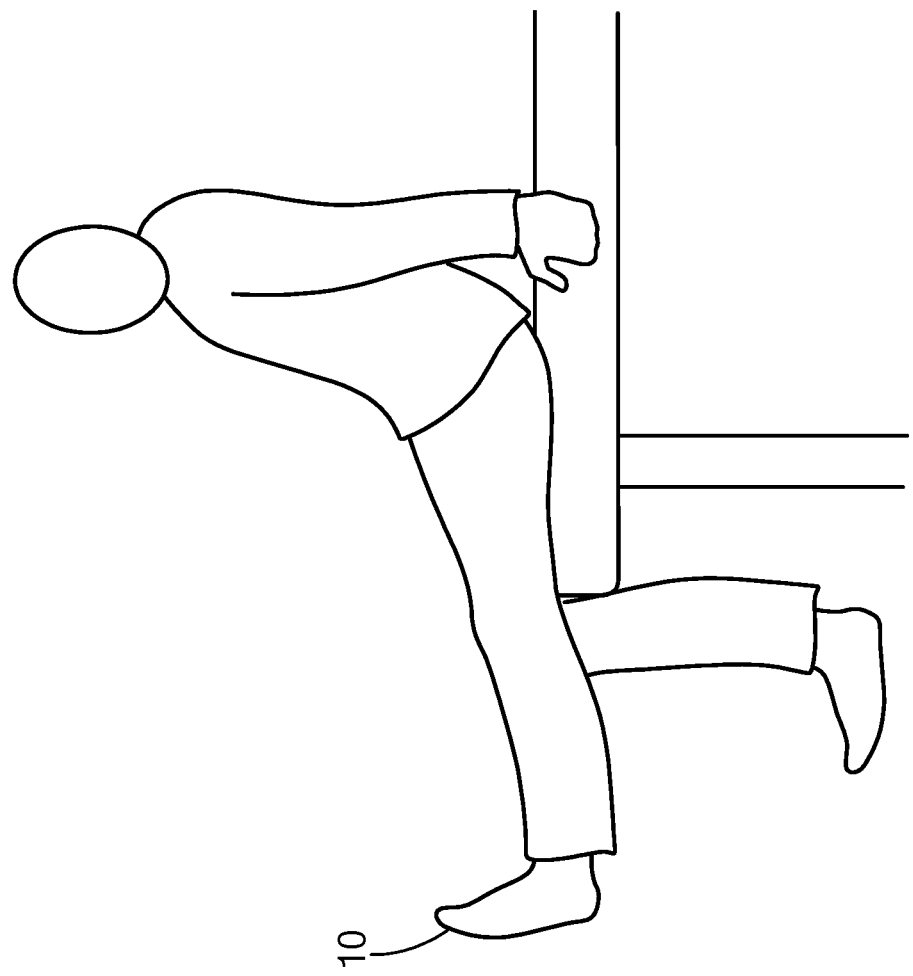
FIG. 2 schematically shows a person using a thermal camera modality to obtain temperature values relating to the foot of a patient.
Figure 2:
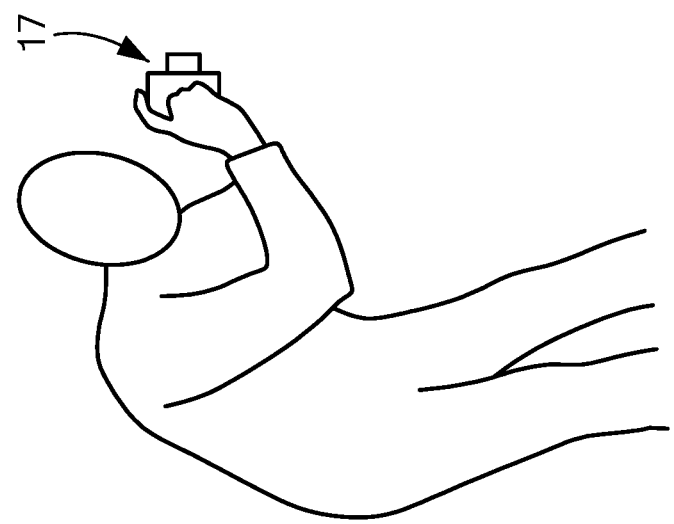

To monitor the health of the patient's foot (discussed in greater detail below), illustrative embodiments use any of a variety of modalities to gather temperature data about a plurality of different locations on the sole of the patient's foot 10. This temperature data provides the core information ultimately used to determine the health of the foot 10. To that end, FIG. 2 schematically shows one modality for evaluating a patient's foot for inflammation, which could indicate an ulcer or a pre-ulcer. In this case, a person (e.g., a healthcare provider or relative of the patient) holds a thermal camera modality ("thermal camera 17") to capture temperature information relating to the sole of the patient's foot.

As known by those in the art, rather than using visible light, a thermal camera (also known as a "thermographic camera," "thermal imaging camera," or an "infrared camera") forms an image of an object using infrared radiation. More specifically, a thermal camera captures the heat signature of an object (e.g., the sole of a foot) in electronic form, effectively determining the temperature across the two-dimensional sole of the foot. Among other things, the thermal camera 17 can be portable/hand-held, as shown in FIG. 2, or part of a larger, more stationary platform.

The person may hold the thermal camera 17 in a fully-constrained manner, a partially-constrained manner, or in an unconstrained manner (i.e., as in FIG. 2). For example, when fully unconstrained and held by the person, the camera 17 may be positioned in free space and thus, be movable in free space with respect to the three axes of the Cartesian Coordinate System, in a polar coordinate system, or other coordinate system. Thus, the thermal camera 17 may translate along the X-axis, the Y-axis, and/or the Z-axis of the Cartesian coordinate system, and rotate about the X-axis, the Y-axis, and the Z-axis of the Cartesian coordinate system. Indeed, the thermal camera 17 may move in any one or more of these manners. Accordingly, although the person may attempt to hold the thermal camera 17 perfectly still, it very well may move in some intended or unintended manner. In fact, when taking two different temperature readings as shown in FIG. 2, the person may have difficulties ensuring the same camera distance and orientation relative to the patient's foot.

When fully-constrained, the thermal camera 17 is substantially immovable relative to the patient's foot. As such, the thermal camera 17 is not movable along or about the noted axes.

When partially-constrained, the thermal camera 17 is substantially unmovable in one or more ways, but still movable in at least one other way. For example, the thermal camera 17 may be set against a flat surface and thus, be substantially stable along the Y-axis (if defined as normal to the ground). Despite this stability, the thermal camera 17 may be movable in other ways, such as translatable along the Z-axis and the X-axis. These and other freedoms of movement can lead to analysis complications when evaluating the foot. Illustrative embodiments aim to mitigate these complications.

Figure 3A:
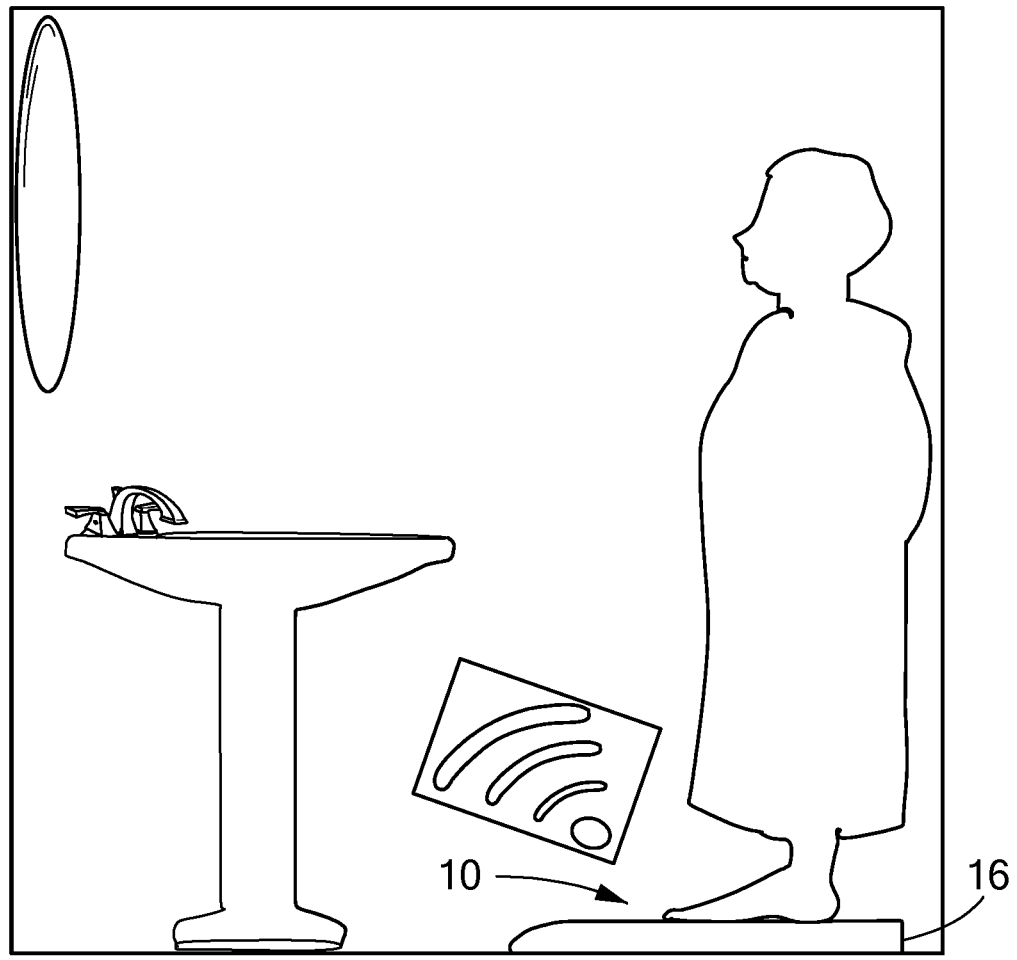
FIG. 3A schematically shows another use and form factor that may be implemented in accordance with illustrative embodiments of the invention.
Figure 3B:
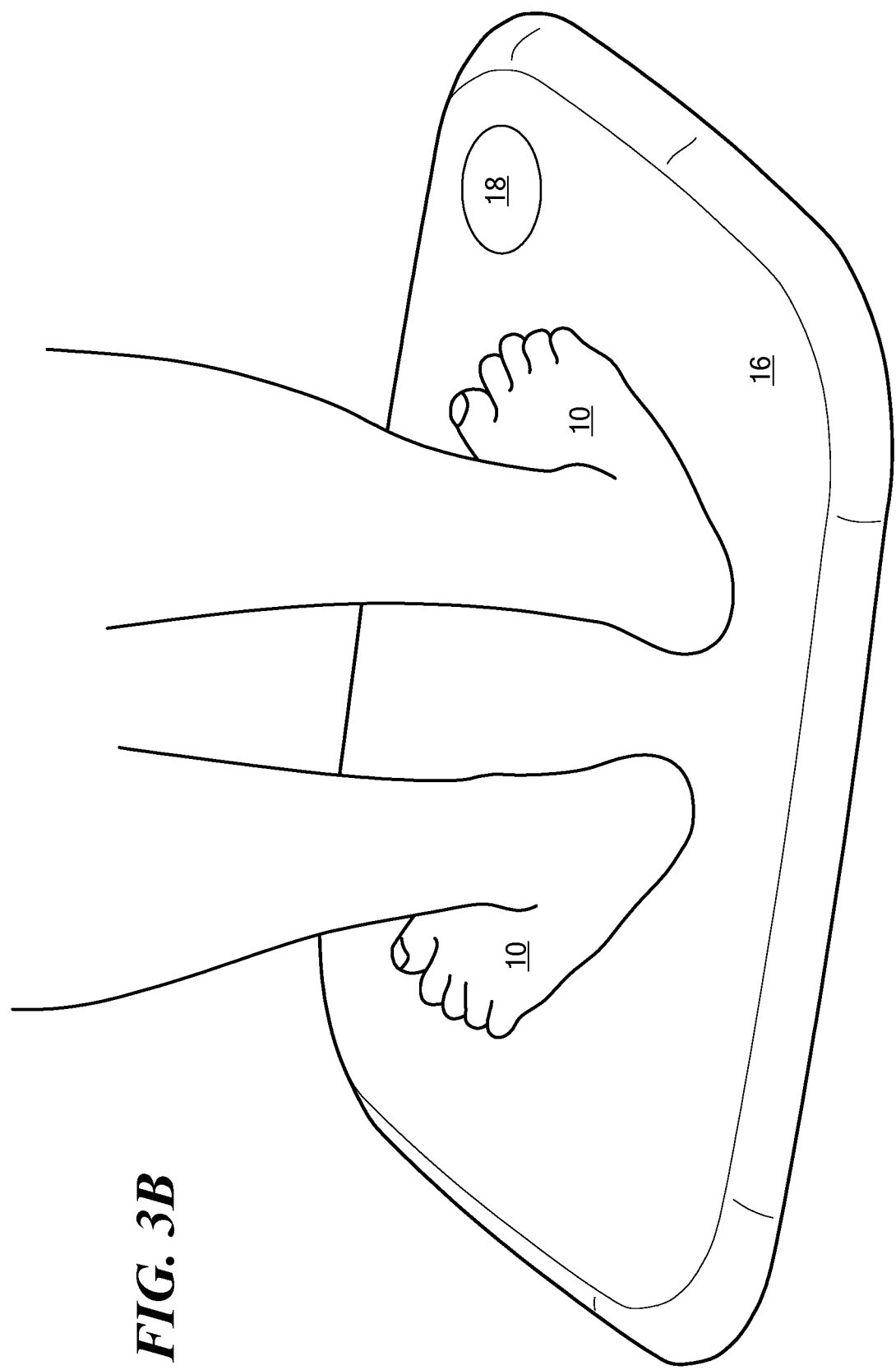
FIG. 3B schematically shows an open platform that may be configured in accordance with illustrative embodiments of the invention.
Figure 3C:
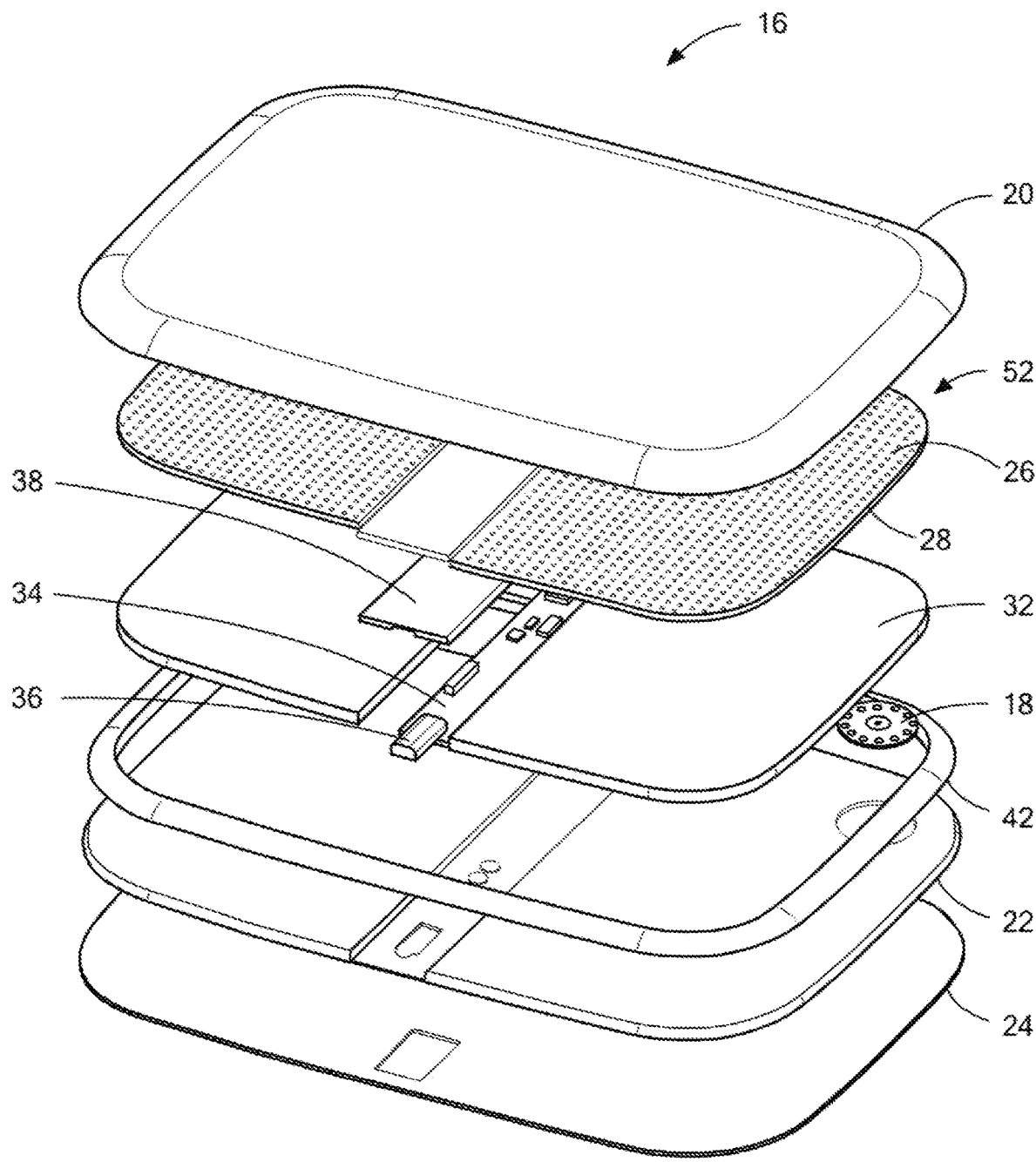
FIG. 3C schematically shows an exploded view of one type of open platform that may be configured in accordance with illustrative embodiments of the invention.

FIGS. 3A and 3B schematically show another modality or form factor, in which a patient steps on an open platform 16 that gathers data about that user's feet 10. In this particular example, the open platform 16 is in the form of a floor mat placed in a location where he the patient regularly stands, such as in front of a bathroom sink, next to a bed, in front of a shower, on a footrest, or integrated into a mattress. As an open platform 16, the patient simply may step on the top sensing surface of the platform 16 to initiate the process. Accordingly, this and other form factors favorably do not require that the patient affirmatively decide to interact with the platform 16. Instead, many expected open platform form factors are configured to be used in areas where the patient frequently stands during the course of their day without a foot covering. Alternatively, the open platform 16 may be moved to directly contact the feet 10 of a patient that cannot stand. For example, if the patient is bedridden, then the platform 16 may be brought into contact with the patient's feet 10 while in bed.

A bathroom mat or rug are but two of a wide variety of different potential open platform form factors. Others may include a platform 16 resembling a scale, a stand, a footrest, a console, a tile built into the floor, or a more portable mechanism that receives at least one of the feet 10. The implementation shown in FIGS. 2A and 2B has a top surface area that is larger than the surface area of one or both of the feet 10 of the patient. This enables a caregiver to obtain a complete view of the patient's entire sole, providing a more complete view of the foot 10.

The open platform 16 (and other modalities, such as the thermal camera modality) also has some indicia or display 18 on its top surface they can have any of a number of functions. For example, the indicia can turn a different color or sound an alarm after the readings are complete, show the progression of the process, or display results of the process. Of course, the indicia or display 18 can be at any location other than on the top surface of the open platform 16, such as on the side, or a separate component that communicates with the open platform 16. In fact, in addition to, or instead of, using visual or audible indicia, the platform 16 may have other types of indicia, such as tactile indicia/feedback, our thermal indicia.

To operate efficiently, the open platform 16 should be configured so that its top surface contacts substantially the entire sole of the patient's foot 10. To that end, the platform 16 has a flexible and movable layer of foam 32 or other material that conforms to the user's foot 10. For example, this layer should conform to the arch of the foot 10. Of course, the sensors 26, printed circuit board 28, and cover 20 also should be similarly flexible and yet robust to conform to the foot 10 in a corresponding manner. Accordingly, the printed circuit board 28 preferably is formed largely from a flexible material that supports the circuit. For example, the printed circuit board 28 may be formed primarily from a flex circuit that supports the temperature sensors 26, or it may be formed from strips of material that individually flex when receiving feet. Alternative embodiments may not have such flexibility (e.g., formed from conventional printed circuit board material, such as FR-4) and thus, produce less effective data.

The rigid base 22 positioned between the foam 32 and the non-skid base 24 provides rigidity to the overall structure. In addition, the rigid base 22 is contoured to receive a motherboard 34, a battery pack 36, a circuit housing 38, and additional circuit components that provide further functionality. For example, the motherboard 34 may contain integrated circuits and microprocessors that control the functionality of the platform 16.

The platform 16 also may have edging 42 and other surface features that improve its aesthetic appearance and feel to the patient. The layers may be secured together using one or more of an adhesive, snaps, nuts, bolts, or other fastening devices.

Rather than using an open platform 16, alternative embodiments may be implemented as a closed platform, such as an insole, a shoe, or a sock that can be regularly worn by a patient, or worn on an as-needed basis. For example, the insole of the patient's shoe or boot may have the functionality for detecting the emergence of a pre-ulcer 14 or ulcer 12, and/or monitoring a pre-ulcer 14 or ulcer 12. The open platform 16 and thermal camera 17 modalities are discussed in greater detail in its parent patent application, U.S. application Ser. No. 13/799,828, which already was incorporated by reference.

Figure 4:
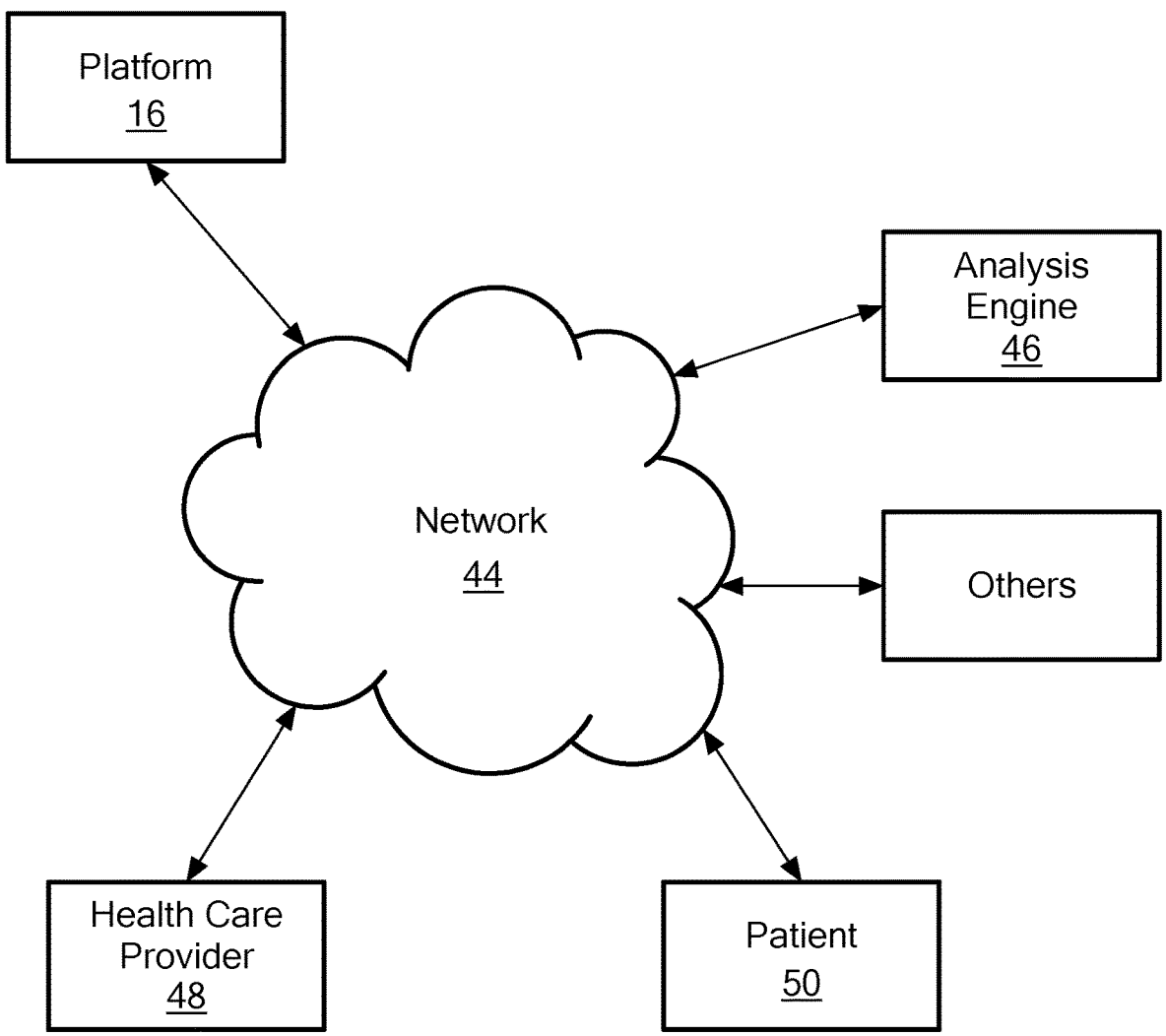
FIG. 4 schematically shows a network implementing of illustrative embodiments of the invention.

Although it gathers temperature and other data about the patient's foot, illustrative embodiments may locate additional logic for monitoring foot health at another location. For example, such additional logic may be on a remote computing device. To that and other ends, FIG. 4 schematically shows one way in which the thermal camera 17, open platform 16, closed platform or other modality (shown schematically in FIG. 4 as "Platform 16" but applicable to other modalities) can communicate with a larger data network 44 in accordance with various embodiments the invention. As shown, the platform 16 may connect with the Internet through a local router, through its local area network, or directly without an intervening device. This larger data network 44 (e.g., the Internet) can include any of a number of different endpoints that also are interconnected. For example, the platform 16 may communicate with an analysis engine 46 that analyzes the thermal data from the platform 16 and determines the health of the patient's foot 10. The platform 16 also may communicate directly with a healthcare provider 48, such as a doctor, nurse, relative, and/or organization charged with managing the patient's care. In fact, the platform 16 also can communicate with the patient (identified in this figure by reference number 50), such as through text message, telephone call, e-mail communication, or other modalities as the system permits.

Figure 5:
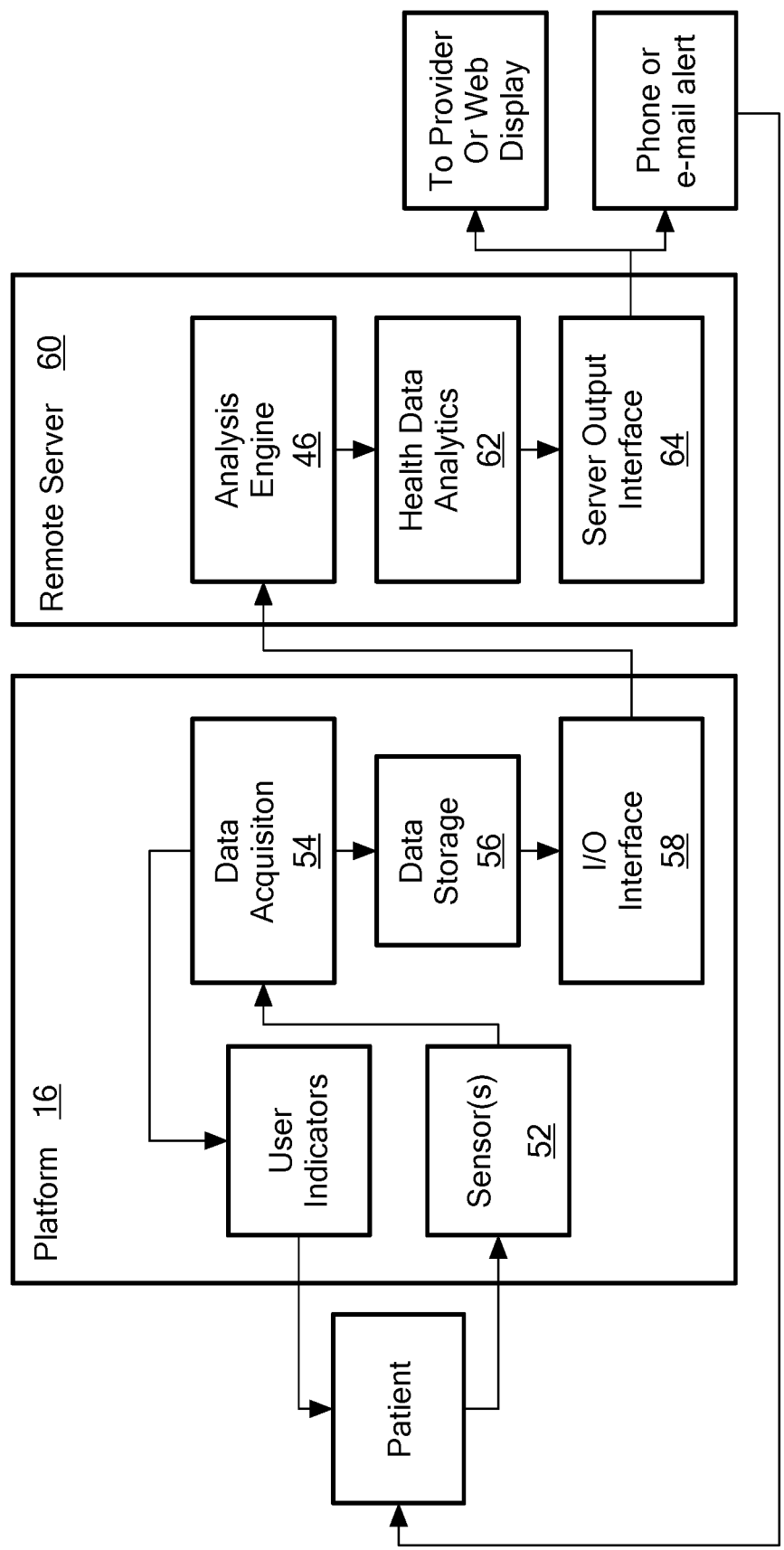
FIG. 5 schematically shows an overview of various components of illustrative embodiments of the invention.

FIG. 5 schematically shows a block diagram of a foot monitoring system, showing the platform 16 and the network 44 with its interconnected components in more detail. As shown, the patient communicates with the platform 16 by communicating its heat signature or thermal information to the sensor(s) 52, such as a thermal collector of the thermal camera 17, or a sensor array of the open platform." A data acquisition block 54, implemented by, for example, a motherboard 34 and circuitry, controls acquisition of the temperature and other data for storage in a data storage device 56. Among other things, the data storage device 56 can be a volatile or nonvolatile storage medium, such as a hard drive, high-speed random-access-memory ("RAM"), and/or solid-state memory. The input/output interface port 40, also controlled by the motherboard and other electronics on the platform 16, selectively transmits or forwards the acquired data from the storage device to the analysis engine 46 on a remote computing device, such as a server 60. The data acquisition block 54 also may control the user indicators/displays 18, which provide feedback to the user through the above mentioned indicia (e.g., audible, visual, or tactile).

As noted above and discussed in greater detail below with regard to FIGS. 7 and 8, the analysis engine 46, on the remote server 60, analyzes the data received from the platform 16 in conjunction with a health data analytics module 62. A server output interface 64 forwards the processed output information/data from the analysis engine 46 and health data analytics module 62 toward others across the network 44, such as to a provider, a web display, or to the user via a phone, e-mail alert, text alert, or other similar way.

This output message may have the output information in its relatively raw form for further processing. Alternatively, this output message may have the output information formatted in a high-level manner for easy review by automated logic or a person viewing the data. Among other things, the output message may indicate the actual emergence of an ulcer 12 or a pre-ulcer 14, the risk of the emergence of an ulcer 12 or a pre-ulcer 14, or simply that the foot 10 is healthy and has no risks of ulcer 12 or pre-ulcer 14. In addition, this output message also may have information that helps an end-user or healthcare provider 48 monitor an ulcer 12 or pre-ulcer 14.

Using a distributed processing arrangement like that shown in FIG. 5 has a number of benefits. Among other things, it permits the platform or modality 16 to have relatively simple and inexpensive components that are unobtrusive to the patient. Moreover, this permits a "software-as-a-service" business model ("SAAS model"), which, among other things, permits more flexibility in the functionality, typically easier patient monitoring, and more rapid functional updates. In addition, the SAAS model facilitates accumulation of patient data to improve analytic capability.

Some embodiments may distribute and physically position the functional components in a different manner. For example, the platform (e.g., the thermal camera 17) may have the analysis engine 46 on its local motherboard. In fact, some embodiments provide the functionality entirely on the modality, such as on the open platform and/or within other components in the local vicinity of the platform 16. For example, all of those functional elements (e.g., the analysis engine 46 and other functional elements) may be within a housing that also contains the thermal camera 17. Accordingly, discussion of a distributed platform is but one of a number of embodiments that can be adapted for a specific application or use.

Figure 6:
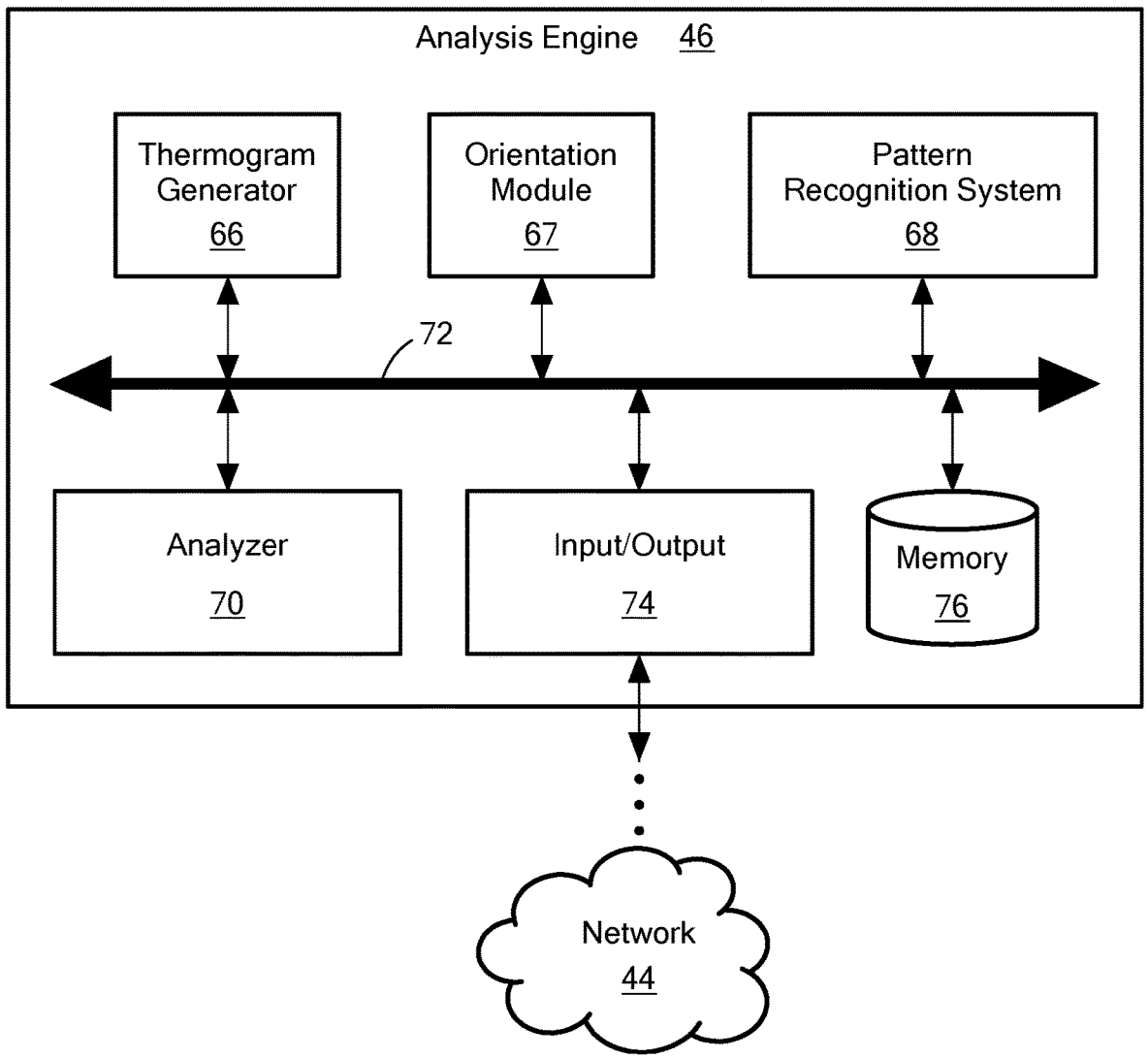
FIG. 6 schematically shows details of a data processing module in accordance with illustrative embodiments of the invention.

Those skilled in the art can perform the functions of the analysis engine 46 (and the other functional modules) using any of a number of different hardware, software, firmware, or other non-known technologies. FIG. 6 shows several functional blocks that, with other functional blocks, may be configured to perform functions of the analysis engine 46. This figure simply shows the blocks and is illustrative of one way of implementing various embodiments, while FIGS. 7 and 8 describe their functions in greater detail.

In summary, the analysis engine 46 of FIG. 6 has a thermogram generator 66 configured to form a thermogram of the patient's foot 10 or feet 10 based on temperature readings from the bottom of the foot 10, and a pattern recognition system 68 configured to determine whether the thermogram presents any of a number of different prescribed patterns. Pattern data, thermograms, and other information may be stored in a local memory 76. As discussed below, if the thermogram presents any of these prescribed patterns, then the foot 10 may be unhealthy in some manner (e.g., having a pre-ulcer 14 or an ulcer 12).

The analysis engine 46 also has an orientation module 67 configured to apply at least one transformation to a thermogram—preferably to align the features of different thermograms—and an analyzer 70 configured to produce the above noted output information, which indicates any of a number of different conditions of the foot 10. For example, the output information may indicate the risk that an ulcer 12 will emerge, the emergence of a pre-ulcer 14 (i.e., the first indication of a pre-ulcer 14), the progression of a known ulcer 12, or the emergence of a new ulcer 12 (i.e., the first indication of any given ulcer 12 to the patient and associated support). Communicating through some interconnect mechanism, such as a bus 72 or network connection, these modules cooperate to determine the status of the foot 10, which may be transmitted or forwarded through an input/output port 74 that communicates with the prior noted parties across the larger data network 44.

As noted above, some or all of these modules may be implemented in hardware, software, firmware, or a combination of hardware and software. For example, some modules may be configured across several integrated circuits (e.g., microprocessors or application specific integrated circuits) on one or more printed circuit boards. Those skilled in the art may select the implementation based on the requirements of their given situation (e.g., availability of resources, additional functions, current technology, etc.).

Figure 7:
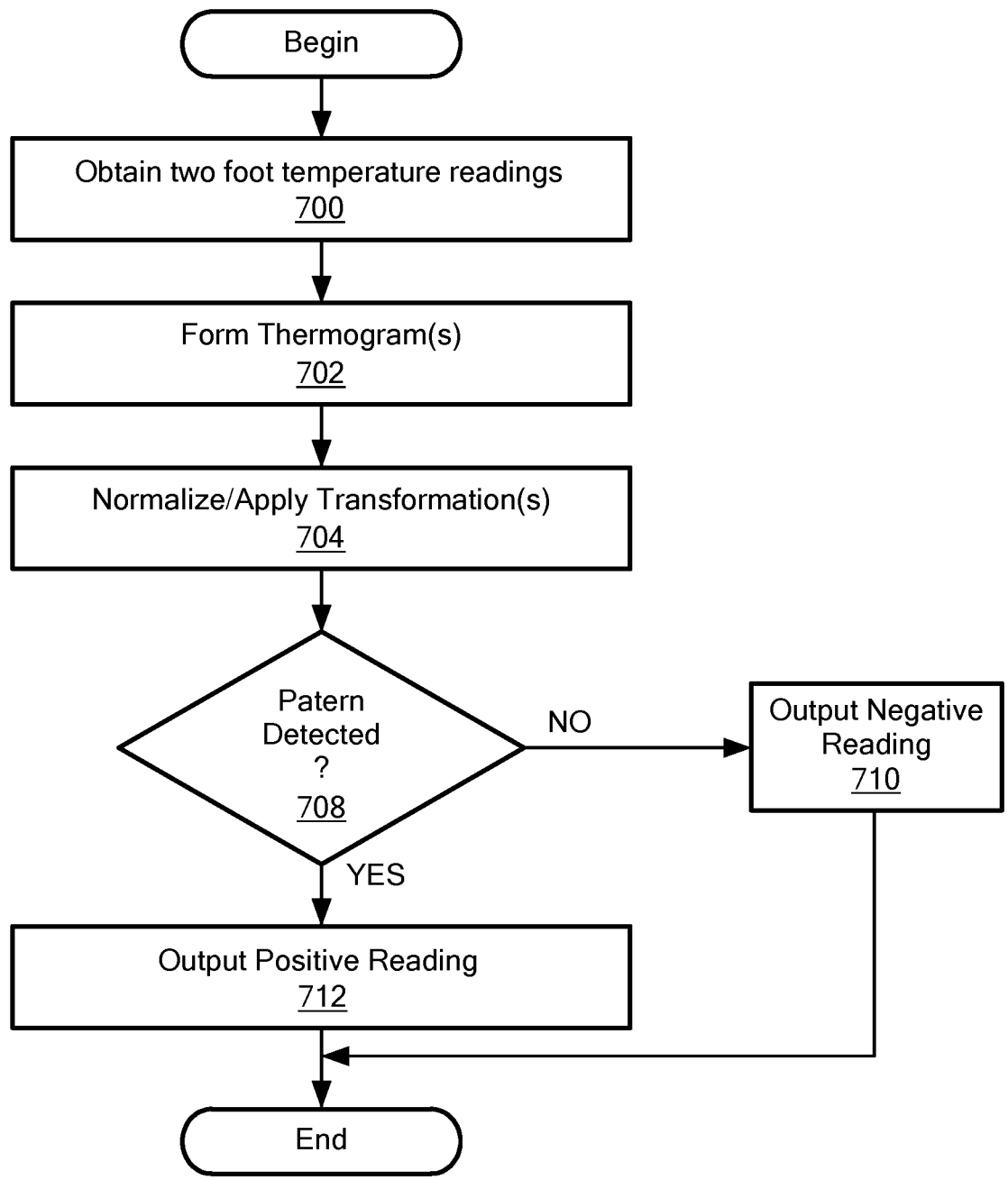
FIG. 7 shows a process of monitoring the health of the patient's foot or feet in accordance with illustrative embodiments the invention.

FIG. 7 shows a process that uses the various components described above in FIGS. 1 through 6 to determine the health of the patient's foot 10. It should be noted that this process is a simplified, high level summary of a much larger process and thus, should not be construed to suggest that only these steps are required. In addition, some of the steps may be performed in a different order than those described below. Although functions and processes of this process are described as being executed by the functional blocks in FIGS. 5 and 6, some embodiments can be executed by other functional components.

The process begins at step 700, in which the temperature gathering modality obtains two foot temperature readings. Specifically, the modality obtains foot temperature information in two different actions. For example, the thermal camera 17 may take a first thermal image of the right foot, and a second thermal image of the left foot. As another example, the thermal camera 17 may take a first thermal image of both feet, and a second thermal image of both feet at a different time, such as the next day. As yet another example, a first thermal camera 17 may take the first thermal image, while a second thermal camera 17 may take the second thermal image. In still a fourth example, the thermal camera 17 may take the first thermal image, while the open platform 16 (i.e., a second modality) may take the second thermal image. These two thermal images may be taken at the same time, or at different times (e.g., seconds, minutes, hours, or days apart). This is in contrast to embodiments that may take thermal images of two feet in a single action (e.g., taking the thermal image of two feet at the same time in the same action with a single thermal camera 17).

Figure 9A:
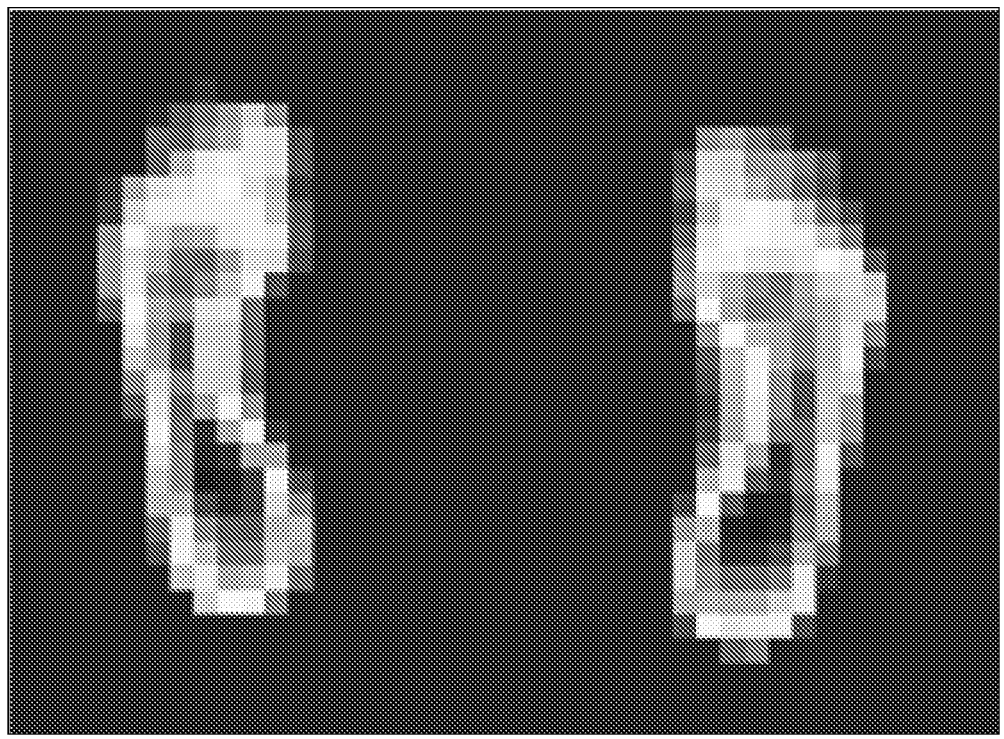
FIGS. 9A-9D schematically show the progression of the thermogram and how it is processed in accordance with one embodiment of the invention.

This step therefore produces a matrix of discrete temperature values across the foot 10 or feet 10. For example, these discrete temperature values may be in the form of discrete pixels of a thermographic image obtained with the thermal camera 17. This temperature data also may have additional meta-data, such as the date and time of obtaining this temperature data. FIG. 9A (discussed below) graphically shows one example of this discrete temperature data for two feet 10 (e.g., using an open platform). As discrete temperature values, this representation does not have temperature information for the regions of the foot 10 between the temperature values. Accordingly, using this discrete temperature data shown in FIG. 9A, the thermogram generator 66 forms two separate thermograms—one thermogram for each foot temperature reading (step 702).

Accordingly, based on the matrix of discrete temperature values, the temperature detection modality, or other functional module, forms a first thermogram and a separate second thermogram of the sole of at least one foot. For example, the first thermogram may represent the left foot, while the second thermogram may represent the right foot. Two separate actions thus were taken to obtain each of the data values used to form the thermograms. As another example, the first thermogram may represent the left foot on a given day, while the second thermogram may represent the left foot the next day. Each of these thermograms has relevant features, such as an outline, a shape, temperature information, prominent anatomical shapes, etc., that ultimately will be used to orient the thermograms (discussed below).

In simple terms, as known by those in the art, a thermogram is a data record made by a thermograph, or a visual display of that data record. A thermograph simply is an instrument that records temperatures (i.e., the platform 16). As applied to illustrative embodiments, a thermograph measures temperatures and generates a thermogram, which is data, or a visual representation of that data, of the spatially-continuous two-dimensional temperature data across some physical region, such as a foot 10. Accordingly, unlike an isothermal representation of temperature data, a thermogram provides a complete, continuous data set/map of the temperatures across an entire two-dimensional region/geography. More specifically, in various embodiments, a thermogram shows (within accepted tolerances) substantially complete and continuous two-dimensional spatial temperature variations and gradients across portions of the sole of (at least) a single foot 10, or across the entire sole of the single foot 10.

Those skilled in the art may form the thermogram in a variety of different manners. For example, the thermogram may be formed by calculating temperature values between some or all of the plurality of discrete temperature values of the foot retrieved by the modality. Among other things, these intermediate temperature values may be calculated using interpolation techniques. Reference is made to the above noted incorporated parent application for some thermogram generation examples, which involves interpolation, re-orienting, and adjusting the baseline temperature. That example may be used separately at least in part with illustrative embodiments discussed below with regard to FIG. 7 and FIG. 8. FIG. 9B schematically shows one example of the thermogram at this stage of the process. This FIG. 3891/1017-should be contrasted with FIG. 9A, which shows a more discrete illustration of the soles of the feet 10.

At this point, the process is considered to have formed the thermogram, which may be stored in memory 76. For effective use, however, it nevertheless still may require further processing. Accordingly, at step 704, the orientation module 67 applies one or more transformations to the two thermograms, thus normalizing/registering the thermograms to a standard coordinate system. Some embodiments may apply the transformations/normalize as the modality collects the data, while other embodiments, such as the one shown in FIG. 7, may apply the transformations/normalize after forming the thermograms. FIG. 8, which is discussed in greater detail below, describes one example of the latter type of normalization. FIG. 9C schematically shows one example of how this step may reorient the thermogram of FIG. 9B.

The position and orientation of the foot 10 on the platform 16 therefore is important when performing this step. For example, when using the open platform 16, to determine the position and orientation of the foot 10, the analysis engine 46 and its thermogram generator 66 simply may contrast the regions of elevated temperature on the platform 16 (i.e., due to foot contact) with those at ambient temperature. Other embodiments may use pressure sensors to form a pressure map of the foot 10.

Figure 9B:
Figure 9C:
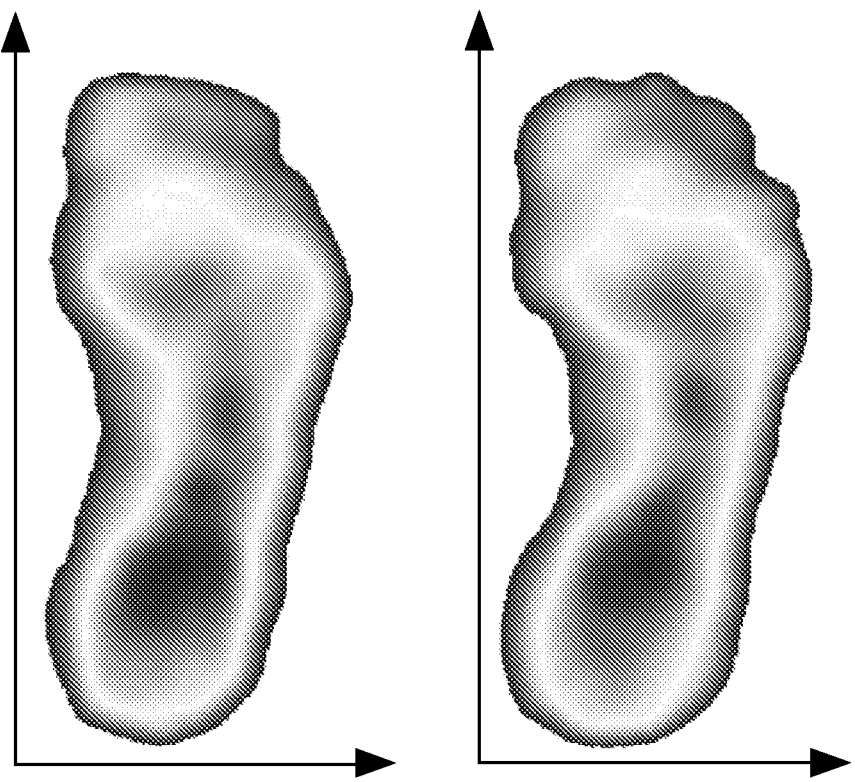
Figure 9D:
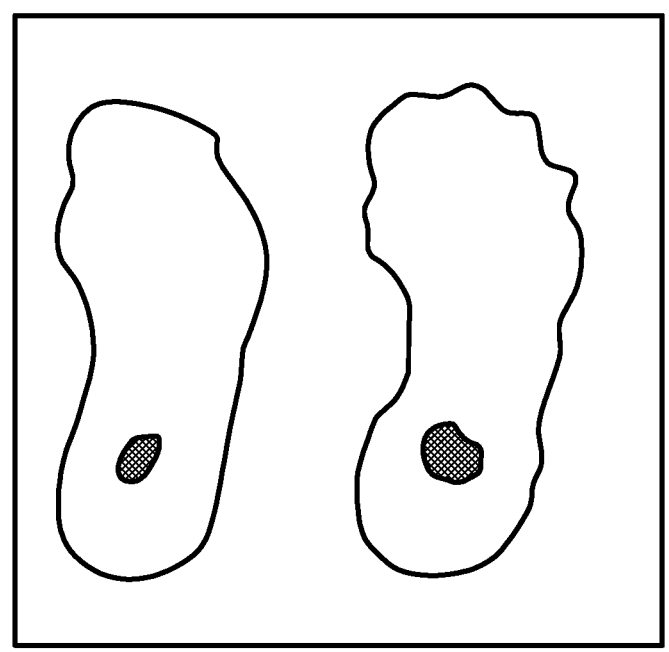

Some embodiments may further modify the thermogram to better contrast warmer portions of the foot 10 against other portions of the foot 10. FIG. 9D schematically shows a thermogram produced in this manner from the thermogram of FIG. 9C. This figure more clearly shows two hotspots on the foot 10 than FIG. 9C. To that end, the process determines the baseline or normal temperature of the foot 10 for each location within some tolerance range. The amount to which the actual temperature of a portion of the foot 10 deviates from the baseline temperature of that portion of the foot 10 therefore is used to more readily show hotspots.

For example, if the deviation is negative, the thermogram may have some shades of blue, with a visual scale of faint blues being smaller deviations and richer blues being larger deviations. In a similar manner, positive deviations may be represented by some shades of red, with a visual scale of faint red being smaller deviations and richer reds being larger deviations. Accordingly, and this example, bright red portions of the thermogram readily show hotspots that may require immediate attention. Of course, other embodiments may use other colors or techniques for showing hotspots. Accordingly, discussion of color coding or specific colors is not intended to limit all embodiments.

Figure 8:
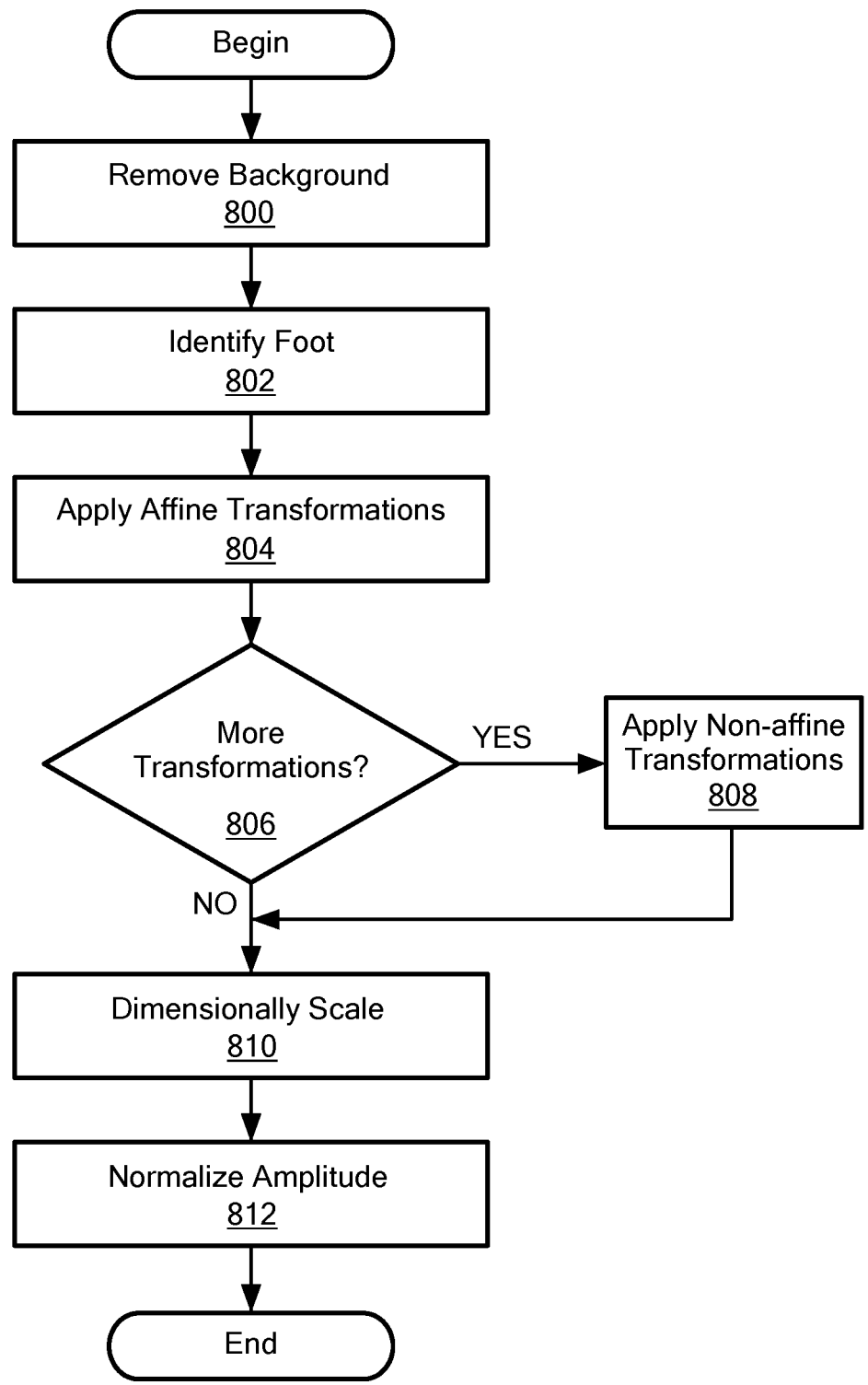
FIG. 8 shows a process of normalizing a thermogram in accordance with illustrative embodiments of the invention.

Briefly moving away from the discussion of FIG. 7, FIG. 8 shows a process of normalizing the two thermograms to a standard coordinate system in accordance with illustrative embodiments of the invention. As with the process of FIG. 7, this process is a simplified process of a potentially longer process. Accordingly, some embodiments may add steps, eliminate steps, or modify steps. Moreover, some steps may be performed in a different order than that discussed.

Before beginning this process, the orientation module 67 receives one or both of the thermograms (e.g., from memory 76 or other means). Indeed, the thermograms can be applied to the standard coordinate system, or the standard coordinate system can be applied to the thermograms. In the latter case, some embodiments may orient the first thermogram to a standard coordinate system, and then coordinate the second thermogram to the first thermogram. In either case, the two thermograms are oriented to effectively and efficiently perform the process of FIG. 7.

The normalization process begins at step 800, which removes background information from both thermograms, leaving a respective single foot for each thermogram. For example, background radiation can be removed using a graph-partitioning method, which examines homogenous regions of the thermogram (in terms of temperature) and segments the regions to minimize the gradient across the segments in the thermogram. Alternatively, some embodiments may use simpler histogram or thresholding techniques, where the background is assumed to have a uniformly lower value than the region of interest (e.g., the feet).

Next, step 802 identifies the foot, such as by forming an outline around the perimeter of the foot in each thermogram. This outline can substantially exactly track the perimeter of the foot, or be in the form of a rectangle about the outline of the foot. Some embodiments may search for fully-enclosed regions with similar principal characteristics (e.g., length, width, or area ratio) to a foot. Alternatively, the normalization process may search the thermogram for a thermometric template of the foot, either generated for a generic subject or using previously-collected data for a specific subject. Among other ways, this search can use optimization techniques to maximize the favorability of the fit by applying affine or non-affine transformations to the template or thermogram.

The process continues by applying one or more appropriate transformations to the thermograms. In this case, as noted in step 804, the process applies one or more affine transformations to each thermogram. In general, as known by those in the art, an affine transformation generally preserves co-linearity (i.e., all points lying on a line initially still lie on a line after transformation) and ratios of distances (e.g., the midpoint of a line segment remains the midpoint after transformation). Geometric contraction, expansion, dilation, reflection, rotation, shear, scaling, similarity transformations, spiral similarities, and translation all may be considered to be affine transformations, as are their combinations. More generally, an affine transformation is a composition of rotations, translations, dilations, and shears.

Illustrative embodiments rotate and/or translate the thermograms, as needed, to a standard coordinate system defined by the principal axis of the foot. Such a technique registers features of the thermogram with the standard coordinate system. For example, one embodiment may register/orient the first thermogram to the standard coordinate system, and then simply register/orient the second thermogram to the first thermogram (effectively registering them to the same standard coordinate system). When registering, the system thus may cause the relevant thermogram to translate and rotate in one or more of pitch, roll, and yaw.

In addition to rotating and translating, step 804 also may mirror and/or align all or part of the thermograms. For example, illustrative embodiments may mirror a left foot by simply rotating its thermogram 180 degrees along its major axis so that it can be aligned with the right foot. Rather than mirroring the entire thermogram, however, some embodiments may mirror only corresponding portions of the thermograms, such as portions known to be most prone to inflammation.

Illustrative embodiments mirror the thermograms as appropriate when comparing the left foot to the right foot. Accordingly, in such cases, step 804 does not mirror a single foot over time—it is unnecessary. To that end, the process may rotate one of the transformations, and then align some or all common portions together. For example, step 804 may rotate the first thermogram, and then align the heels of both thermograms together to align other corresponding portions of the sole. It also should be noted that step 804 may align thermograms whether comparing left and right foot thermograms, or when comparing thermograms of the same foot over time.

Alternative embodiments may omit the affine transformations of step 804.

Step 806 then determines if more transformations are necessary. If so, then the process may continue to step 808, which can apply non-affine transformations to one or both of the thermograms. As such, these transformations generally do not preserve thermogram co-linearity (i.e., all points lying on a line initially still lie on a line after transformation) and ratios of distances. For example, some embodiments may dimensionally stretch, deform, represent a three-dimensional space in two-dimensions, or otherwise modify one or both thermograms in a corresponding manner. Among other ways, some embodiments may use non-affine transformations in a series to approximate a single affine transformation. In that latter case, some embodiments may skip the affine transformations.

The process then may dimensionally scale one or both thermograms (step 810). For example, both feet may not be the same size or shape, or the thermograms of the feet may not be the same size or shape. This may become an issue with the thermal camera 17, in which its distance from the sole and its rotation relative to the foot varies. This step thus may map both thermograms to a common shape, such as the shape of a foot, or even a shape that does not resemble a foot. For example, step 810 may stretch and compress the thermogram to the shape of a circle. This step preferably is executed internally to the orientation module 67 and thus, not displayed on a display device. Other steps, however, may display the thermograms as they are processed.

The process may conclude by normalizing the amplitude of the temperature signal across the entire thermogram. This may be important when using a closed platform having an elevated temperature (e.g., a shoe after exercise). Illustrative embodiments may normalize the amplitude signal in a number of manners, such as by subtracting the temperatures across two thermograms, or determining the temperature based on some prescribed temperature. Among other things, the prescribed temperature may include the mean temperature across the thermogram, the median temperature across the thermogram, or the background temperature. Continuing with the above example, when using the mean temperature, the thermogram may show that a local temperature is 1 degree C. above the mean temperature.

The amplitude also may be normalized over time to remove extraneous trends or correct for harmonic fluctuations due to time-of-day or time-of-month, or to eliminate or remove unwanted artifacts in the signal due to exogenous factors, such as the patient's activity or basal temperature.

Now that the thermogram generator 66 has generated the two normalized thermograms, the process returns to FIG. 7. Specifically, the pattern recognition system 68 determines if the thermograms present or show any of a number of prescribed patterns, and the analyzer 70 analyzes the pattern to determine if there are hotspots (step 708). In particular, as noted, an elevated temperature at a particular portion of the foot 10 may be indicative or predictive of the emergence and risk of a pre-ulcer 14 or ulcer 12 in the foot 10. For example, temperature deviations of about 2 degrees C. or about 4 degrees F. in certain contexts can suggest emergence of an ulcer 12 or pre-ulcer 14. Temperature deviations other than about two degrees C. also may be indicative of a pre-ulcer 14 or ulcer 12 and thus, 2 degrees C. and 4 degrees F. are discussed by example only. Accordingly, various embodiments analyze the thermograms to determine if the geography of the foot 10 presents or contains one or more of a set of prescribed patterns indicative of a pre-ulcer 14 or ulcer 12. Such embodiments may analyze the visual representation of the thermograph, or just the data otherwise used to generate and display a thermograph image—without displaying the thermograph.

A prescribed pattern may include a temperature differential over some geography or portion of the foot 10 or feet 10. To that end, various embodiments contemplate different patterns that compare at least a portion of the foot 10 against other foot data. Among other things, those comparisons may include the following:

1. A comparison of the temperature of the same portion/spot of the same foot 10 at different times (i.e., a temporal comparison of the same spot),
2. A comparison of the temperatures of corresponding portions/spots of the patient's two feet 10 at the same time or at different times, and/or
3. A comparison of the temperature of different portions/spots of the same foot 10 at the same time or at different times.

Figure 10A:
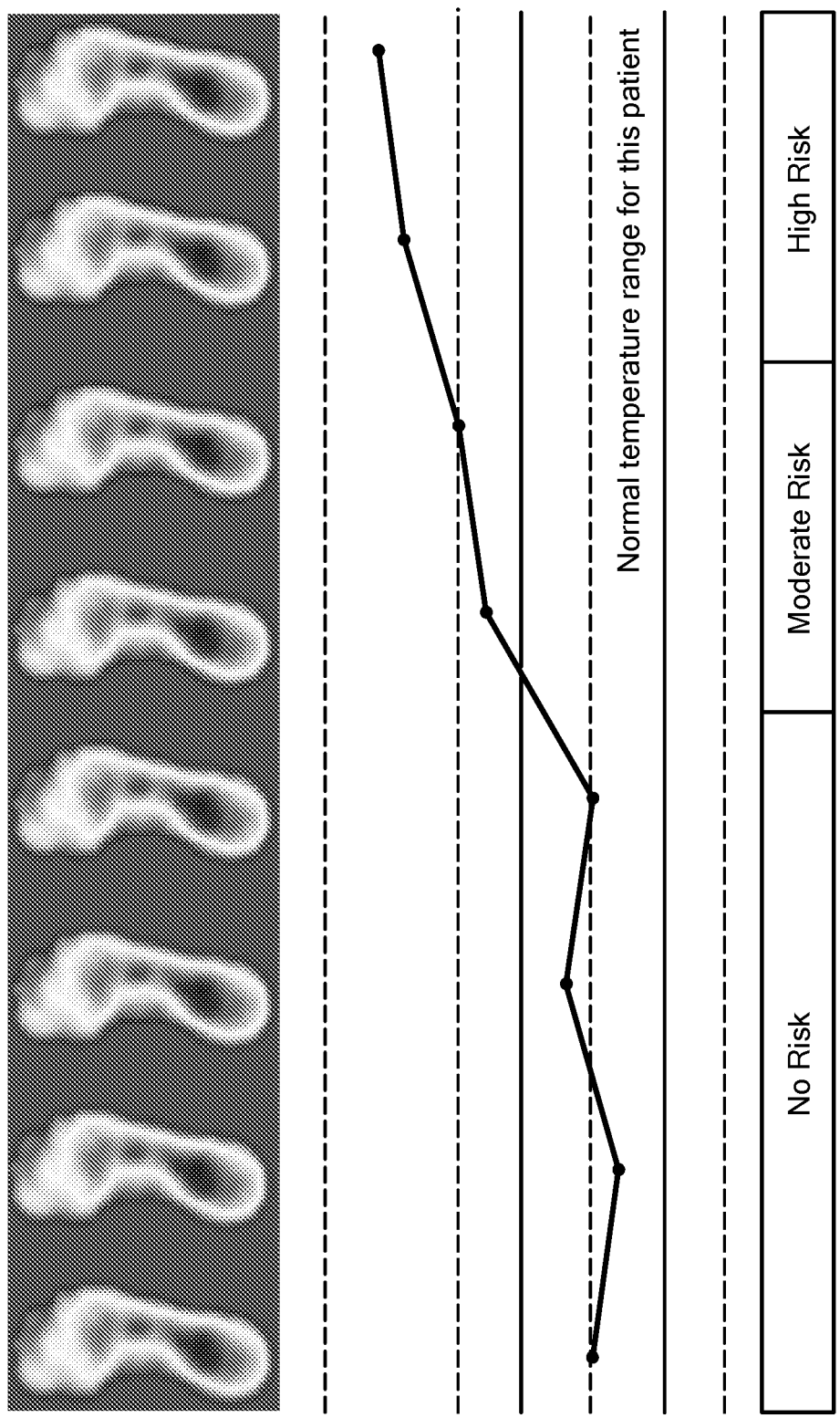
FIGS. 10A and 10B schematically show two different types of patterns that may be on the soles of a patient's foot indicating an ulcer or pre-ulcer.

As an example of the first comparison, the pattern may show a certain region of a foot 10 has a temperature that is 4 F higher than the temperature at that same region several days earlier. FIG. 10A schematically shows one example of this, in which a portion of the same foot 10—the patient's left foot 10, has a spot with an increased risk of ulceration.

Figure 10B:
Figure 10B:

As an example of the second comparison, the pattern may show that the corresponding portions of the patient's feet 10 have a temperature differential that is 4 degrees F. FIG. 10B schematically shows an example of this, where the region of the foot 10 on the left (the right foot 10) having a black border is hotter than the corresponding region on the foot 10 on the right (the left foot 10).

As an example of the third comparison, the pattern may show localized hotspots and peaks within an otherwise normal foot 10. These peaks may be an indication of pre-ulcer 14 or ulcer 12 emergence, or increased risk of the same, which, like the other examples, alerts caregiver and patient to the need for more vigilance.

Accordingly, if no pattern indicative of relevant inflammation is detected, then the output produces a negative reading or message (step 710), indicating no or minimal risk. Conversely, if such a pattern is detected, then the process may conclude at step 712, producing an output reading indicating a risk of ulceration or pre-ulcer (or similar indication). The output reading may include the risk of an ulcer 12 emerging anywhere on the foot 10, or at a particular location on the foot 10. This risk may be identified on a scale from no risk to maximum risk. Indeed, some embodiments include evaluation of inflammation at various stages, from no inflammation, to pre-ulcer, to full ulcer. See the incorporated patent applications for some examples of such stages.

Of course, various embodiments may make similar comparisons while analyzing the thermograms for additional patterns. For example, similar to the third comparison, the pattern recognition system 68 may have a running average of the temperature of the geography of the entire foot 10 over time. For any particular spot on the foot 10, this running average may fall within a normal range between a high temperature and a low temperature for that set of thermograms over a period of time. Accordingly, data indicating that the temperature at that given spot is outside of the normal range may be predictive of a pre-ulcer 14 or an ulcer 12 at that location.

Some embodiments may use machine learning and advanced filtering techniques to ascertain risks and predictions, and to make the comparisons. More specifically, advanced statistical models may be applied to estimate the current status and health of the patient's feet 10, and to make predictions about future changes in foot health. State estimation models, such as a switching Kalman filters, can process data as they become available and update their estimate of the current status of the user's feet 10 in real-time. The statistical models can combine both expert knowledge based on clinical experience, and published research (e.g., specifying which variables and factors should be included in the models) with real data gathered and analyzed from users. This permits models to be trained and optimized based on a variety of performance measures.

Models can be continually improved as additional data is gathered, and updated to reflect state-of-the-art clinical research. The models also can be designed to take into account a variety of potentially confounding factors, such as physical activity (e.g., running), environmental conditions (e.g., a cold floor), personal baselines, past injuries, predisposition to developing problems, and problems developing in other regions (e.g., a rise in temperature recorded by a sensor 26 may be due to an ulcer 12 developing in a neighboring region measured by a different sensor). In addition to using these models for delivering real-time analysis of users, they also may be used off-line to detect significant patterns in large archives of historical data. For example, a large rise above baseline temperature during a period of inactivity may precede the development of an ulcer 12.

Alternative embodiments may configure the pattern recognition system 68 and analyzer 70 to perform other processes that identify risk and emergence, as well as assist in tracking the progressions of ulcers 12 and pre-ulcers 14. For example, if there is no ambient temperature data from a thermogram prior to the patient's use of the platform 16, then some embodiments may apply an Otsu filter (or other filter) first to the high resolution thermogram to identify regions with large temperature deviations from ambient. The characteristics of these regions (length, width, mean temperature, etc. . . . ) then may be statistically compared to known distributions of foot characteristics to identify and isolate feet 10. The right foot thermogram may be mirrored and an edge-alignment algorithm can be employed to standardize the data for hotspot identification.

Two conditions can be evaluated independently for hotspot identification. The first condition evaluates to true when a spatially-localized contralateral thermal asymmetry exceeds a pre-determined temperature threshold for a given duration. The second condition evaluates to true when a spatially-localized ipsilateral thermal deviation between temporally successive scans exceeds a pre-determined temperature threshold for a given duration. The appropriate durations and thermal thresholds can be determined from literature review or through application of machine learning techniques to data from observational studies. In the latter case, a support vector machine or another robust classifier can be applied to outcome data from the observational study to determine appropriate temperature thresholds and durations to achieve a desired balance between sensitivity and specificity.

Illustrative embodiments have a set of prescribed patterns against which the pattern recognition system 68 and analyzer 70 compare to determine foot health. Accordingly, discussion of specific techniques above are illustrative of any of a number of different techniques that may be used and thus, are not intended to limit all embodiments of the invention.

The output of this analysis can be processed to produce risk summaries and scores that can be displayed to various users to trigger alerts and suggest the need for intervention. Among other things, state estimation models can simulate potential changes in the user's foot 10 and assess the likelihood of complications in the future. Moreover, these models can be combined with predictive models, such as linear logistic regression models and support vector machines, which can integrate a large volume and variety of current and historical data, including significant patterns discovered during off-line analysis. This may be used to forecast whether the user is likely to develop problems within a given timeframe. The predictions of likelihood can be processed into risk scores, which also can be displayed by both users and other third parties. These scores and displays are discussed in greater detail below.

Figure 11A:
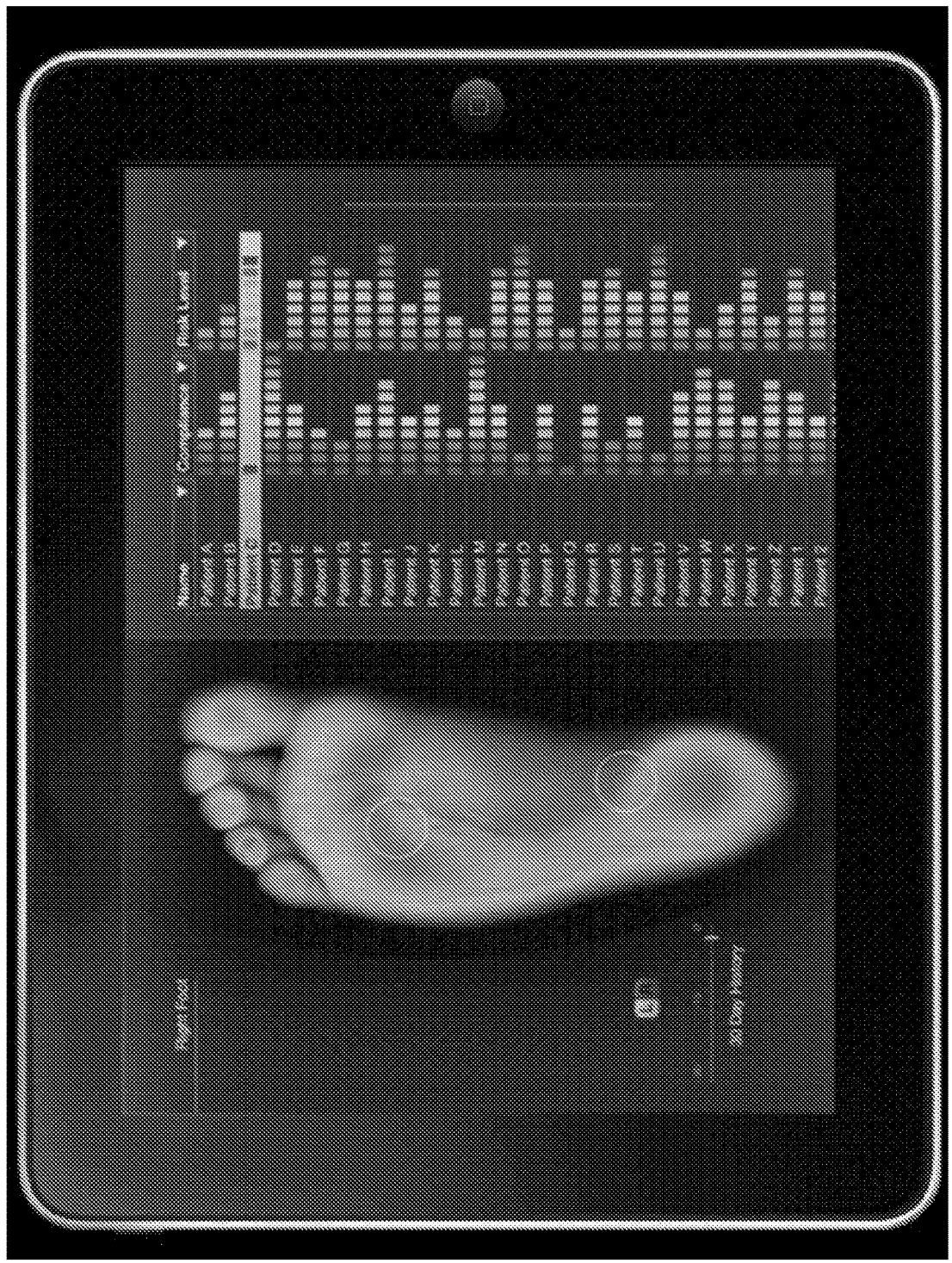
FIGS. 11A and 11B schematically show two different user interfaces that may be displayed in accordance with illustrative embodiments of the invention.
Figure 11B:
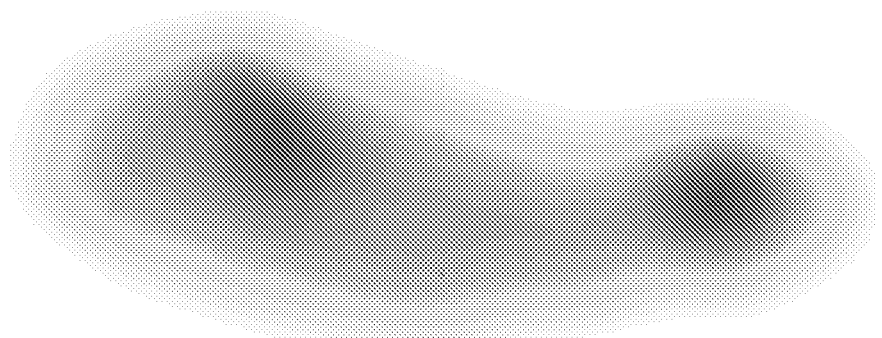

FIG. 11A shows one example of the output information in a visual format with a scale ranking the risk of ulcer emergence. The scale in this example visually displays de-identified patients (i.e., Patient A to Patient 2) as having a certain risk level of developing the foot ulcer 12. The "Risk Level" column shows one way of graphically displaying the output information, in which more rectangles indicate a higher risk of ulcer 12. Specifically, in this example, a single rectangle may indicate minimal or no risk, while rectangles filling the entire length of that table entry may indicate a maximum risk or fully emerged ulcer 12. Selection of a certain patient may produce an image of the foot 10 with a sliding bar showing the history of that patient's foot 10. FIG. 11B schematically shows a similar output table in which the risk level is characterized by a percentage from zero to hundred percent within some time frame (e.g., days). Patient C is bolded in this example due to their 80 percent risk of the emergence of an ulcer 12.

The output table thus may provide the caregiver or healthcare provider with information, such as the fact that Patient B has a 90 percent probability that he/she will develop a foot ulcer 12 in the next 4-5 days. To assist in making clinical treatment decisions, the clinician also may access the patient's history file to view the raw data.

Other embodiments produce output information indicating the emergence of a pre-ulcer 14 at some spot on the foot 10. As known by those skilled in the art, a pre-ulcer 14 may be considered to be formed when tissue in the foot 10 is no longer normal, but it has not ruptured the top layer of skin. Accordingly, a pre-ulcer 14 is internal to the foot 10. More specifically, tissue in a specific region of the foot 10 may not be receiving adequate blood supply and thus, may need more blood. When it does not receive an adequate supply of blood, it may become inflamed and subsequently, become necrotic (i.e., death of the tissue). This creates a weakness or tenderness in that region of the foot 10. Accordingly, a callous or some event may accelerate a breakdown of the tissue, which ultimately may rupture the pre-ulcer 14 to form an ulcer 12.

Illustrative embodiments may detect the emergence of a pre-ulcer 14 in any of a number of manners described above. For example, the system may compare temperature readings to those of prior thermograms, such as the running average of the temperature at a given location. This comparison may show an elevated temperature at that spot, thus signaling the emergence of a new pre-ulcer 14. In more extreme cases, this may indicate the actual emergence of a new ulcer 12.

The emergence or detection of a pre-ulcer 14 can trigger a number of other preventative treatments that may eliminate or significantly reduce the likelihood of the ultimate emergence of an ulcer 12. To that end, after learning about a pre-ulcer 14, some embodiments monitor the progression of the pre-ulcer 14. Preferably, the pre-ulcer 14 is monitored during treatment in an effort to heal the area, thus avoiding the emergence of an ulcer 12. For example, the caregiver may compare each day's thermogram to prior thermograms, thus analyzing the most up to date state of the pre-ulcer 14. In favorable circumstances, during a treatment regimen, this comparison/monitoring shows a continuous improvement of the pre-ulcer 14, indicating that the pre-ulcer 14 is healing. The output information therefore can have current and/or past data relating to the pre-ulcer 14, and the risk that it poses for the emergence of an ulcer 12.

Sometimes, patients may not even realize that they have an ulcer 12 until it has become seriously infected. For example, if the patient undesirably does not use the foot monitoring system for a long time, he/she may already have developed an ulcer 12. The patient therefore may undergo an analysis of his/her foot/feet to produce output information indicating the emergence of an ulcer 12. To that end, the analyzer 70 may have prior baseline thermogram (i.e., data) relating to this patient's foot 10 (showing no ulcer), and make a comparison against that baseline data to determine the emergence of an actual ulcer 12. In cases where the data is questionable about whether it is an ulcer 12 or a pre-ulcer 14, the caregiver and/or patient nevertheless may be notified of the higher risk region of the foot 10 which, upon even a cursory visual inspection, should immediately reveal the emergence of an ulcer 12.

Some embodiments manually or automatically notify the relevant people about the health of the patient's foot 10. These notifications or messages (a type of "risk message") may be in any of a number of forms, such as a telephone call, a text message, e-mail, and data transmission, or other similar mechanism. For example, the system may forward an e-mail to a healthcare provider indicating that the right foot 10 of the patient is generally healthy, while the left foot 10 has a 20 percent risk of developing an ulcer 12, and a pre-ulcer 14 also has emerged on a specified region. Armed with this information, the healthcare provider may take appropriate action, such as by directing the patient to stay off their feet 10, use specialized footwear, soak their feet 10, or immediately check into a hospital.

Accordingly, illustrative embodiments take advantage of the continuous data provided by two thermograms to ascertain various risks to foot health. In addition, such embodiments also monitor the foot 10 using an easy to follow regimen and form factor that encourages patient compliance. Early detection can assist in avoiding foot ulcers 12, while late detection can alert patients to yet undiscovered ulcers 12, which can then be effectively treated.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as preprogrammed hardware elements (e.g., application specific integrated circuits, FPGAs, and digital signal processors), or other related components.

In an alternative embodiment, the disclosed apparatus and methods (e.g., see the various flow charts described above) may be implemented as a computer program product (or in a computer process) for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium.

The medium may be either a tangible medium (e.g., optical or analog communications lines) or a medium implemented with wireless techniques (e.g., WIFI, microwave, infrared or other transmission techniques). The medium also may be a non-transient medium. The series of computer instructions can embody all or part of the functionality previously described herein with respect to the system. The processes described herein are merely exemplary and it is understood that various alternatives, mathematical equivalents, or derivations thereof fall within the scope of the present invention.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the larger network 44 (e.g., the Internet or World Wide Web). Of course, some embodiments of the invention may be implemented as a combination of both software (e.g., a computer program product) and hardware. Still other embodiments of the invention are implemented as entirely hardware, or entirely software.

Although the above discussion discloses various exemplary embodiments of the invention, it should be apparent that those skilled in the art can make various modifications that will achieve some of the advantages of the invention without departing from the true scope of the invention.

Some embodiments may apply to the following innovations:

1. An innovation method comprising:
   providing a temperature detection modality;
   receiving a two-dimensional array of discrete temperature values from the temperature detection modality, the two-dimensional array representing a plurality of discrete temperature values of the sole of at least one foot;
   calculating temperatures between a plurality of adjacent discrete temperature values to form a thermogram of the sole of each of the at least one foot, the thermogram forming a substantially continuous set of two-dimensional temperature values across the sole of the at least one foot;
   controlling a device to orient the thermogram to a standard coordinate system;
   determining, at any location within the thermogram and after orienting, whether the thermogram presents one of a plurality of patterns indicative of ulceration or pre-ulceration; and
   producing output information indicating the result of the determination of whether the thermogram presents one of the plurality of patterns.
2. The method of innovation 1 wherein the temperature modality comprises an open platform.
3. The method of innovation 1 wherein the temperature modality comprises a thermal camera.
4. The method of innovation 1 wherein the device comprises orientation logic.
5. The method of innovation 4 wherein the orientation logic comprises one or more of a processor and an integrated circuit.
6. The method of innovation 1 further comprising visually displaying the thermogram.
7. The method of innovation 1 wherein temperatures calculated between the plurality of adjacent discrete temperature values are mathematically calculated approximate temperature values.
8. The method of innovation 7 wherein calculating temperatures between a plurality of adjacent discrete temperature values comprises interpolating between at least two adjacent discrete temperature values to determine the mathematically calculated approximate temperature values.

9. The method of innovation 8 wherein the interpolation produces an analog equation that can determine the temperature at any region between at least two of the plurality of adjacent discrete temperature values.

10. The method of innovation 9 wherein the two-dimensional array of discrete temperature values comprises a graphical image having a two-dimensional array of pixels, the pixels being color-coded based on the discrete temperature values.

11. The method of innovation 10 wherein the device is automated to orient the thermogram without human interaction.

12. The method of innovation 11 wherein the standard coordinate system includes a Cartesian or polar coordinate system.

13. The method of innovation 12 further comprising buffering the two-dimensional array of discrete temperature values from the temperature detection modality before controlling the device to orient; and storing the oriented thermogram in memory.

14. The method of innovation 13 wherein the modality comprises an open platform comprises a substrate for receiving the at least one foot, and a plurality of temperature sensors that are stationary relative to the substrate.

15. The method of innovation 1 further comprising receiving additional data associated with the two-dimensional array of discrete temperature values, the additional data including information relating to at least one of the date and time the temperature values were obtained, and metadata related to the foot biology.

16. The method of innovation 1 wherein controlling the device to orient comprises retrieving a prior thermogram from memory, and using the orientation of the prior thermogram to orient the thermogram.

17. The method of innovation 1 further comprising normalizing the amplitude of the two-dimensional array of discrete temperature values for a given pair of feet against a prescribed value.

18. The method of innovation 18 wherein the prescribed value comprises one of the mean temperature across the sole of the given pair of feet, the median temperature across the sole of the given pair of feet, a temperature not associated with the given pair of feet.

19. The method of innovation 1 further comprising mirroring the thermograms of two feet of the same person.

20. The method of innovation 1 further comprising dimensionally scaling the thermogram before determining.

21. The method of innovation 1 wherein the two-dimensional array of discrete temperature values comprises temperature values spaced away from the sole of the at least one foot.

What is claimed is:

1. A method of predicting emergence of an ulcer on at least a right foot or a left foot of a patient, each foot having a sole and an arch, the method comprising:
providing an open platform having a substrate having an array of temperature sensors comprising a plurality of temperature sensors, and comprising a flexible material configured to conform the array of temperature sensors substantially to said arch of at least one foot, said open platform further including at least one user indicator configured to provide feedback indicia to the patient during use;
generating, using the plurality of temperature sensors of the array substantially conformed to the arch of each foot, a first and a second plurality of discrete temperature data values of the soles of the feet of the patient, the first plurality of discrete temperature data values having first features, the second plurality of discrete temperature data values having second features,
the first plurality of discrete temperature data values representing a sole of the left foot of the patient and the second plurality of discrete temperature data values represents a sole of the right foot of the patient;
providing one or more processors;
receiving a baseline temperature profile of at least one foot of the patient, the baseline temperature profile being for a foot of the patient showing no ulcer;
determining, by at least one of the one or more processors, whether at least one of the first and second plurality of discrete temperature data values presents one of a plurality of patterns indicative of foot inflammation of the respective sole of at least one of the left and right feet of the patient, said determining comprising comparing at least one of the first and at least one of the second plurality of discrete temperature data values against the baseline temperature profile of the patient; and
producing, by at least one of the one or more processors and based on said determining, output information predicting emergence of an ulcer on at least one of the two feet of the patient; and
displaying the output information on a display.

2. The method of claim 1, further comprising, prior to determining whether at least one of the first and second plurality of discrete temperature data values presents one of a plurality of patterns indicative of an ulcer emerging on the respective sole of at least one of the left and right feet of the patient:
controlling at least one of the one or more processors to apply at least one transformation to one or both of the first and second plurality of discrete temperate data values to align the first features of the first plurality of discrete temperature data values with corresponding second features of the second plurality of discrete temperature data values.

3. The method as defined by claim 2 wherein the at least one transformation comprises at least one affine transformation.

4. The method as defined by claim 3 wherein the at least one affine transformation comprises at least one of reflection, rotation, scaling and translation.

5. The method as defined by claim 2 wherein the at least one transformation further comprises a non-affine transformation to at least one of the first and second plurality of discrete temperature data values.

6. The method as defined by claim 2 the at least one transformation aligns the first features and the second features to a common coordinate system, said controlling comprising changing the orientation, relative to the common coordinate system, of at least one of the first and second plurality of discrete temperature data values for one or more of X-axis translation, X-axis rotation, Y-axis translation, Y-axis rotation, Z-axis translation, and Z-axis rotation.

7. The method as defined by claim 2 wherein the flexible material is configured to conform the array of temperature sensors substantially to said arch of each of the patient's feet.

8. The method as defined by claim 2 wherein said controlling comprises retrieving the first plurality of discrete temperature data values from memory in an orientation, and using the orientation of the first plurality of discrete temperature data values to orient the second plurality of discrete temperature data values.

9. The method as defined by claim 1 further comprising normalizing the amplitude of the first and second plurality of discrete temperature data values against a common value.

10. A system for predicting emergence of an ulcer on at least a right foot or a left foot of a patient, each foot having a sole and an arch, the system comprising:
  an open platform configured to generate a first and a second plurality of discrete temperature data values of the soles of feet of the patient, the open platform having a substrate having an array of temperature sensors comprising a plurality of temperature sensors, and comprising a flexible material configured to conform the array of temperature sensors substantially to said arch of each foot;
  the first plurality of discrete temperature data values having first features, the second plurality of discrete temperature data values having second features,
  the first plurality of discrete temperature data values representing a sole of the left foot of the patient and the second plurality of discrete temperature data values represents a sole of the right foot of the patient;
  a pattern recognition system configured:
    to receive a baseline temperature profile of at least one foot of the patient, the baseline temperature profile being for a foot of the patient showing no ulcer, and
    to determine whether at least one of the first and second plurality of discrete temperature data values presents one of a plurality of patterns indicative of foot inflammation of the respective sole of at least one of the left and right feet of the patient, and configured
    to determine whether at least one of the first and second plurality of discrete temperature data values presents one of a plurality of patterns predictive of emergence of an ulcer by comparing at least one of the first and at least one of the second plurality of discrete temperature data values against the baseline temperature profile of the patient; and
  an analyzer operatively coupled with the pattern recognition system, the analyzer being configured to produce output information indicating a result of the determination of whether the first and second plurality of discrete temperature data values present one of the plurality of patterns predictive of emergence of an ulcer;
  wherein the system is further configured to display the output information on a display.

11. The system as defined by claim 10, further comprising:
  an orientation module operatively coupled with the input, the orientation module being configured to apply at least one transformation to at least the first plurality of discrete temperature data values to align the first features of first plurality of discrete temperature data values with corresponding second features of the second plurality of discrete temperature data values.

12. The system as defined by claim 11, wherein the at least one transformation comprises at least one affine transformation.

13. The system as defined by claim 12, wherein the at least one affine transformation comprises at least one of reflection, rotation, scaling and translation.

14. The system as defined by claim 11, wherein the at least one transformation comprises a non-affine transformation.

15. The system as defined by claim 11, wherein the at least one transformation aligns the first features and the second features to a common coordinate system, said controlling comprising changing the orientation, relative to the common coordinate system, of at least one of the first and second plurality of discrete temperature data values for one or more of X-axis translation, X-axis rotation, Y-axis translation, Y-axis rotation, Z-axis translation, and Z-axis rotation.

\* \* \* \* \*